(12) United States Patent
Yadav et al.

(10) Patent No.: US 7,816,006 B2
(45) Date of Patent: *Oct. 19, 2010

(54) NON-STOICHIOMETRIC NANOMATERIAL COMPOSITIONS WITH DISTINCTIVE SHAPE AND MORPHOLOGY

(75) Inventors: Tapesh Yadav, Tucson, AZ (US); Clayton Kostelecky, Longmont, CO (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/811,628

(22) Filed: Mar. 29, 2004

(65) Prior Publication Data

US 2004/0180203 A1 Sep. 16, 2004

Related U.S. Application Data

(60) Continuation of application No. 10/449,278, filed on May 30, 2003, now Pat. No. 6,830,822, which is a division of application No. 10/150,722, filed on May 17, 2002, now Pat. No. 6,602,595, which is a division of application No. 09/274,517, filed on Mar. 23, 1999, now Pat. No. 6,344,271, application No. 10/811,628, which is a continuation-in-part of application No. 09/790,036, filed on Feb. 20, 2001, now Pat. No. 6,933,331, which is a division of application No. 09/083,893, filed on May 22, 1998, now Pat. No. 6,228,904, and a continuation-in-part of application No. 08/739,257, filed on Oct. 30, 1996, now Pat. No. 5,905,000, which is a continuation-in-part of application No. 08/730,661, filed on Oct. 11, 1996, now Pat. No. 5,952,040, which is a continuation-in-part of application No. 08/706,819, filed on Sep. 3, 1996, now Pat. No. 5,851,507, and a continuation-in-part of application No. 08/707,341, filed on Sep. 3, 1996, now Pat. No. 5,788,738.

(60) Provisional application No. 60/107,318, filed on Nov. 6, 1998, provisional application No. 60/110,442, filed on Dec. 1, 1998, provisional application No. 60/049,077, filed on Jun. 9, 1997, provisional application No. 60/069,935, filed on Dec. 17, 1997, provisional application No. 60/079,225, filed on Mar. 24, 1998.

(51) Int. Cl.
*B32B 5/16* (2006.01)

(52) U.S. Cl. .............. 428/402; 428/407; 977/762; 977/783; 977/810; 977/811

(58) Field of Classification Search .............. 428/402, 428/407; 977/DIG. 1, 762, 783, 810, 811; 257/E23.075, E23.166
See application file for complete search history.

(56) References Cited

U.S. PATENT DOCUMENTS 5,984,997 A * 11/1999 Bickmore et al. ............ 75/343

(Continued)

OTHER PUBLICATIONS

"Discovery could lead to new ways to create nano-fibers and wires", Purdue University, Nov. 2003.*

(Continued)

*Primary Examiner*—H. (Holly) T Le

(57) ABSTRACT

Nanoscale materials with domain sizes less than 100 nanometers and unusual shapes and morphologies are disclosed. A broad approach for manufacturing oxide and non-oxide nanomaterials with aspect ratio different than 1.0 is presented. Methods for engineering and manufacturing nanomaterials' size, shape, surface area, morphology, surface characteristics, surface composition, distribution, and degree of agglomeration are discussed. The methods taught includes the use of surfactants, dispersants, emulsifying agents in order to prepare precursors, which are then processed into novel nanoscale particle morphologies.

29 Claims, 2 Drawing Sheets

U.S. PATENT DOCUMENTS

| | | | | |
|---|---|---|---|---|
| 6,156,428 | A * | 12/2000 | Gibson | 428/402 |
| 6,344,271 | B1 * | 2/2002 | Yadav et al. | 428/402 |
| 6,465,543 | B1 * | 10/2002 | Alexandre et al. | 523/213 |
| 6,602,595 | B2 * | 8/2003 | Yadav et al. | 428/323 |
| 6,632,528 | B1 * | 10/2003 | Clough | 428/402 |
| 6,830,822 | B2 * | 12/2004 | Yadav | 428/552 |
| 6,855,749 | B1 * | 2/2005 | Yadav et al. | 523/105 |
| 6,916,872 | B2 * | 7/2005 | Yadav et al. | 524/430 |

OTHER PUBLICATIONS

Khabashesku et al., "Carnonitride nanomaterials, Thin Films, and Solids", Research News, Rice University, Houston, TX.*

Shao-pai Lee, Yu-Wen Chen, "Catalytic Properties of Ni-B and Ni-P ultrafine materials", Research Article, National Central University, Chinese Taipei.*

Liu et al, "Synthesis of GaP nanowires with Ga2O3 coating", Applied Physics A: Materials Science & Processing, Sep. 2004.*

Xin et al, "Formation of self-assembling CdSe quantum dots on ZnSe by molecular beam epitaxy", Applied pHysics Letters, vol. 69 (25) pp. 3884-3886, Dec. 6, 1996.*

Thomas Swan & Co, "New Type of nanotube Made of Gold or Silver Created", Feb. 2004.*

Loh et al, "Growth of boron nitride nanotubes and iron nanowires from the liquid flow of FeB nanoparticles", Dec. 2003.*

Jose-Yacaman, "Maya Blue Paint: An Ancient Nanostructured Material", Science, vol. 273, Jul. 12, 1996, pp. 223-225.*

Chiang et al, "Nonstoichiometry and Electrical Conductivity of Nanocrystalline CeO2-x", Journal of Electroceramics 1:1, 7-14, 1997.*

Xuchuan Jiang, Thurston Herricks, and Younan Xia, CuO Nanowires Can be Synthesized by Heating Copper Substrates in Air, Nano Letters, Published on Web Oct. 24, 2002, vol. 2, No. 12, Dec. 2002.

Yugang Sun, Byron Gates, Brian Mayers, and Younan Xia, Crystalline Silver Nanowires by Soft Solution Processing, Nano Letters, Published on Web Jan. 3, 2002, 2002, vol. 2, No. 2, 165-168.

Hai-Feng Zhang, Alice C. Dohnalkova, Chong-Min Wang, James S. Young, Edgar C. Buck, and Lai-sheng Wang, Lithium-Assisted Self-Assembly of Aluminum Carbide Nanowires and Nanoribbons, Nano Letters, Published on Web Dec. 14, 2001; 2002, vol. 2, No. 2, 105-108.

William E. Buhro and Vicki L. Colvin, Semiconductor Nanocrystais Shape Matters, Nature Materials, vol. 2, Mar. 2003.

Deli Wang and Charles M. Lieber, Inorganic Materials Nanocrystais branch out, Nature Materials, vol. 2, Jun. 2003.

Yiying Wu, Rong Fan, and Peidong Yang, Block-by-Block Growth of Single-Crystalline SI/SiGe Superlattice Nanowires, Nano Letters, Published on Web Jan. 19, 2002, 2002, vol. 2, No. 2, 83-86.

Hyun S. Myung, Jeon G. Han, and Jin H. Boo, A Study on the Synthesis and formation behavior of nanostructured TiN films by copper doping, Surface and Coatings Technology, 177-178 (2004) 404-408.

J. Schoonman, Nanostructured Materials in Solid State Ionics, 135 (2000) 5-19.

Richard Lane, Benjamin Craig and Wade Babcock, Materials Engineering with Nature's Building Blocks, APMTIAC, 2002 (http://amptiac.alionscience.com/pdf/materialease/2002MaterialEase17.pdf).

Othon Adamoplous, et al., The Characterisation and Reactivity of Nanostructured cerium-copper-oxide composites for environmental catalysis, Materials Research Society, Symp. Proc., vol. 676 (2001).

* cited by examiner

XRD spectra of the indium tin oxide nanopowder

NON-STOICHIOMETRIC NANOMATERIAL COMPOSITIONS WITH DISTINCTIVE SHAPE AND MORPHOLOGY

RELATED APPLICATIONS

The present application is a continuation of U.S. patent application Ser. No. 10/449,278 filed on May 30, 2003 entitled "INORGANIC COLORS AND RELATED TECHNOLOGY" now U.S. Pat. No. 6,830,822 which is a division of U.S. patent application Ser. No. 10/150,722 filed on May 17, 2002 entitled "NANOTECHNOLOGY FOR INKS AND DOPANTS" now U.S. Pat. No. 6,602,595 which is a divisional of U.S. patent application Ser. No. 09/274,517 filed on Mar. 23, 1999 entitled "MATERIALS AND PRODUCTS USING NANOSTRUCTURED NON-STOICHIOMETRIC SUBSTANCES" now U.S. Pat. No. 6,344,271 which claims the benefit of provisional application No. 60/107,318, filed Nov. 6, 1998, entitled "MATERIALS AND PRODUCTS USING NANOSTRUCTURED NON-STOICHIOMETRIC MATERIALS," and which claims the benefit of provisional application No. 60/110,442 filed Dec. 1, 1998 all of which are assigned to the assignee of the present invention and which are incorporated herein by reference.

The present application is also a continuation-in-part of U.S. patent application Ser. No. 09/790,036 titled "NANOTECHNOLOGY FOR DRUG DELIVERY, CONTRAST AGENTS AND BIOMEDICAL IMPLANTS" filed on Feb. 20, 2001 now U.S. Pat. No. 6,933,331 which is a divisional of application Ser. No. 09/083,893 now U.S. Pat. No. 6,228,904 filed on May 22, 1998, which is incorporated herein by reference and which claims the benefit of U.S. Provisional applications Nos. 60/049,077 filed on Jun. 9, 1997, 60/069,935 filed on Dec. 17, 1997, and 60/079,225 filed on Mar. 24, 1998. U.S. Pat. No. 6,228,904 is a continuation-in-part of U.S. patent application Ser. No. 08/739,257, filed Oct. 30, 1996, now U.S. Pat. No. 5,905,000, titled NANOSTRUCTURED ION CONDUCTING SOLID ELECTROLYTES, which is a continuation-in-part of U.S. Ser. No. 08/730,661, filed Oct. 11, 1996, now U.S. Pat. No. 5,952,040 titled "PASSIVE ELECTRONIC COMPONENTS FROM NANO-PRECISION ENGINEERED MATERIALS" which is a continuation-in-part of U.S. Ser. No. 08/706,819, filed Sep. 3, 1996, now U.S. Pat. No. 5,851,507 titled "INTEGRATED THERMAL PROCESS FOR THE CONTINUOUS SYNTHESIS OF NANOSCALE POWDERS" and U.S. Ser. No. 08/707,341, filed Sep. 3, 1996, now U.S. Pat. No. 5,788,738 titled "METHOD OF PRODUCING NANOSCALE POWDERS BY QUENCHING OF VAPORS".

BACKGROUND OF THE INVENTION

1. Field of the Invention

The invention relates to non-stoichiometric substances and more particularly to nanostructured non-stoichiometric substances and products incorporating such substances.

2. Relevant Background

Most compounds are prepared as stoichiometric compositions, and numerous methods of preparing substances for commercial use are motivated in objective to create stoichiometric compounds. For example, producers of titania fillers, copper oxide catalysts, titanate dielectrics, ferrite magnetics, carbide tooling products, tin oxide sensors, zinc sulfide phosphors, and gallium nitride electronics all seek stoichiometric compositions ($TiO_2$, $CuO$, $BaTiO_3$, $NiFe_2O_4$, $TiC$, $SnO_2$, $ZnS$, and $GaN$, respectively).

Those skilled in the art will note that conventional powders of oxides and other compounds, when exposed to reducing atmospheres (e.g. hydrogen, forming gas, ammonia, and others) over a period of time, are transformed to non-stoichiometric materials. However, the time and cost of doing this is very high because the inherent diffusion coefficients and gas-solid transport phenomena are slow. This has made it difficult and uneconomical to prepare and commercially apply stable non-stoichiometric forms of materials to useful applications.

Limited benefits of non-stoichiometric materials have been taught by others; for example, Sukovich and Hutcheson in U.S. Pat. No. 5,798,198 teach a non-stoichiometric ferrite carrier. Similarly, Menu in U.S. Pat. No. 5,750,188 teaches a method of forming a thin film of non-stoichiometric luminescent zinc oxide. The film is a result of a thermodynamically favored defect structure involving non-stoichiometric compositions where the non-stoichiometric deviation is in parts per million.

A very wide variety of pure phase materials such as polymers are now readily available at low cost. However, low cost pure phase materials are somewhat limited in the achievable ranges of a number of properties, including, for example, electrical conductivity, magnetic permeability, dielectric constant, and thermal conductivity. In order to circumvent these limitations, it has become common to form composites, in which a matrix is blended with a filler material with desirable properties. Examples of these types of composites include the carbon black and ferrite mixed polymers that are used in toners, tires, electrical devices, and magnetic tapes.

The number of suitable filler materials for composites is large, but still limited. In particular, difficulties in fabrication of such composites often arise due to issues of interface stability between the filler and the matrix, and because of the difficulty of orienting and homogenizing filler material in the matrix. Some desirable properties of the matrix (e.g., rheology) may also be lost when certain fillers are added, particularly at the high loads required by many applications. The availability of new filler materials, particularly materials with novel properties, would significantly expand the scope of manufacturable composites of this type.

SUMMARY OF THE INVENTION

This invention includes several methods of making non-stoichiometric submicron and nanostructured materials and devices from both stoichiometric and non-stoichiometric precursors. This invention also includes methods of making stoichiometric materials and devices from non-stoichiometric precursors. In one aspect, the invention includes an improved sintering technique utilizing submicron non-stoichiometric powders. The invention also includes a variety of other applications for submicron non-stoichiometric materials, including catalysis, photonic devices, electrical devices and components, magnetic materials and devices, sensors, biomedical devices, electrochemical products, and energy and ion conductors.

In one aspect, this invention includes a variety of methods of producing a non-stoichiometric material. According to one method, a submicron powder of a stoichiometric material is transformed into a non-stoichiometric powder. The submicron powder may also be a nanopowder. If desired, the submicron non-stoichiometric powder may be sintered into a bulk substance.

According to another method, a non-stoichiometric submicron material is produced by quenching a high-temperature vapor of a precursor material to produce a non-stoichiometric submicron powder. A vapor stream of the high temperature vapor flows from an inlet zone, and this stream is passed through a convergent means to channel the vapor stream through an area where flow is restricted by controlling the cross-section of the flowing stream. The vapor stream is channeled out of the flow restriction through a divergent means to an outlet pressure which is smaller than the inlet pressure. This quenches the vapor stream. The inlet and outlet pressures are maintained, creating a pressure differential between them. The pressure differential and the cross-section of the flow restriction are adapted to produce a supersonic flow of the vapor stream. This method may further comprise sintering the resulting powder.

According to yet another method, a nanoscale starting material comprising more than one element is provided. At least one of these elements is an electropositive element. A dopant element with valency different than the electropositive element is added, and the mixture is heated to a selected temperature, preferably greater than the solid state reaction temperature, for a time sufficient to allow intermingling of the dopant element and the given electropositive element.

According to still another method, two nanopowders are mixed in a ratio selected to produce a desired non-stoichiometric composition. The first nanopowder comprises a plurality of materials, and the second comprises a subset of those materials. The materials comprising the first nanopowder may be metallic, semimetallic, non-metallic, or any combination thereof. The mixture is heated in a selected atmosphere to a temperature to produce a solid state reaction. The atmosphere may participate in the solid state reaction. This invention also includes the materials produced via the above methods.

In another aspect, this invention includes a submicron non-stoichiometric material where the value for a selected physical property of the submicron non-stoichiometric material is greater than 10% different from that for a stoichiometric form of the submicron non-stoichiometric material. Alternately, the relative ratios of the components of the material differ by more than 1% from the stoichiometric values, preferably 2% from the stoichiometric values, and more preferably 5%. The material may be a nanomaterial or a nanopowder.

This invention also includes a submicron material wherein a domain size of the material is less than 500 nm, and the material is non-stoichiometric. Preferably, the domain size is less than 100 nm. Alternately, a domain size may be less than 5 times the mean free path of electrons in the given material, or the mean domain size may be less than or equal to a domain size below which the substance exhibits 10% or more change in at least one property when the domain size is changed by a factor of 2. The material may be a powder or a nanopowder.

In another aspect, this invention includes a method of determining the non-stoichiometry of a material. A stoichiometric form of the material and the material whose stoichiometry is to be ascertained (the "unknown" material) are heated separately in a reactive atmosphere to 0.5 times the melting point of the material. The weight change per unit sample weight for the unknown material is monitored. In addition, the weight change per unit sample weight of the unknown material is compared to the weight change per unit sample weight of the known material.

In another aspect, this invention includes a method of conducting combinatorial discovery of materials where non-stoichiometric forms of materials are used as precursors.

In another aspect, this invention includes a method of making a non-stoichiometric nanoscale device by fashioning a non-stoichiometric nanoscale material into a device. Alternately, a device is fashioned from a stoichiometric material and the stoichiometric material converted into a non-stoichiometric form. The stoichiometric material may be an electrochemical material, a photonic material, or a magnetic material. The non-stoichiometric material may be electroded; and the electrode may comprise a non-stoichiometric material. This invention also includes stoichiometric devices with non-stoichiometric electrodes. The non-stoichiometric materials may further be nanomaterials.

In another aspect, this invention includes a method of producing a stoichiometric material from a non-stoichiometric powder. The powder is processed into the shape desired for a stoichiometric material and further processed to produce stoichiometric ratios among its components. This invention also includes a method of producing a stoichiometric device via the same method.

In another aspect, this invention also includes an improved method of producing sintered materials. A submicron stoichiometric powder is formed into a green body. The green body is sintered at a selected densification rate and a selected temperature which are lower than those required to sinter larger, stoichiometric powders. This method may further comprise converting the sintered material to a stoichiometric form or stabilizing the non-stoichiometric sintered material by the addition of a protective coating, secondary phase, or stabilizer. In this method, the submicron non-stoichiometric powder may also be nanopowders.

This invention also includes a method of producing an improved catalyst. A nanopowder comprising indium tin oxide and alumina are pressed into pellets. The pellets are reduced in a reducing atmosphere to form a catalyst which can promote the formation of hydrogen from 12% methanol vapor at 250° C. This invention also includes the improved catalyst prepared by this method.

In another aspect, this invention includes a method of producing an improved photonic material. A high-temperature vapor of a precursor material is quenched from a gas stream comprising hydrogen and argon to produce a non-stoichiometric submicron powder such that the absorption of selected wavelengths is more than doubled with respect to that of a stoichiometric from of the precursor. In this method, the precursor material may be stoichiometric ITO; the selected wavelengths would be greater than 500 nm. In addition, this invention includes an improved non-stoichiometric photonic material produced by this process and exhibiting enhanced absorption of selected wavelengths of electromagnetic radiation in comparison to a stoichiometric form of the material.

In another aspect, this invention includes a method of producing an improved electric device. Titanium oxide nanopowders are heated in an ammonia atmosphere to produce a non-stoichiometric oxynitride of titanium. The resulting device may also be part of an electrical conductor. This invention also includes the improved electrical device produced by this method.

This invention also includes a variety of methods of making improved magnetic materials and devices. According to one method, a nickel zinc ferrite material is sintered to near theoretical density and heated in a reducing atmosphere at an elevated temperature such that the resulting material exhibits higher magnetic loss than the stoichiometric starting material. The atmosphere may comprise 5% H-95% Ar and the temperature may be 800° C.

According to another method, a mixture of two stoichiometric nanopowders is produced from manganese ferrite and nickel zinc ferrite powders. These two powders are pressed together, sintered, and wound. The method may further comprise pressing the two nanopowders with a binder, preferably 5% Duramax. This invention also includes the magnetic devices and materials produced by these methods.

In another aspect, this invention includes methods of making a non-stoichiometric resistor. In one method, the resistor is produced from a stoichiometric submicron material and transformed to a non-stoichiometric form. In another method, the resistor is produced from non-stoichiometric $SiC_x$ nanopowders. The nanopowders are sonicated in polyvinyl alcohol and screened printed on a alumina substrate. The resulting resistor element is to produce a resistor having a resistance less than 1 megaohm. Platinum or silver dopants may be added to the sonicated mixture. This invention also includes the improved resistors produced via these methods and arrays of resistors produced via these methods.

In another aspect, this invention also includes a method of producing an improved sensor device. A non-stoichiometric nanopowder is sonicated in a solvent to form a slurry. The slurry is brushed onto screen-printed electrodes and allowed to dry at to remove the solvent. A dissolved polymer may also be included in the slurry. The screen-printed electrodes may be gold electrodes on an alumina substrate. The screen may be made from stainless steel mesh at least 8×10 inches in size, with a mesh count of 400, a wire diameter of 0.0007 inches, a bias of 45°, and a polymeric emulsion of 0.0002 inches.

In another aspect, this invention includes an improved sensor device prepared from a screen printable paste. A nanopowder and polymer are mechanically mixed; a screen-printing vehicle is added to the mixture and further mechanically mixed. The mixture is milled and screen-printed onto prepared electrodes. The paste is allowed to level and dry. This invention also includes the improved sensor devices produced by the above processes.

This invention, in a further aspect, includes a method of making an improved biomedical orthopedic device. A feed powder comprising a non-stoichiometric Ti—Ta—Nb—Zr alloy is milled under non-oxidizing conditions. The milled powder is mixed with a binder dissolved in a solvent and allowed to dry. The mixture is then pressed and incorporated into a biomedical device. This invention also includes a biomedical material comprising a non-stoichiometric submicron powder. In addition, this invention includes a biomedical material produced by this process wherein the powder is a nanopowder.

This invention, in another aspect, includes a method of preparing an improved electronic component. A non-stoichiometric nanoscale material is mixed with a screen printing material and the resulting paste screen-painted on an alumina substrate. The paste is wrapped up and dried on a heated plate and further screen-printed with silver-palladium to form a conducting electrode. The silver-palladium is dried rapidly on a heated plate and the two films co-fired.

In another aspect, this invention includes an improved electrochemical material comprising a submicron non-stoichiometric material. The material has excess Gibbs free energy in comparison to larger grained materials. In addition, the material exhibits increased solute diffusion, lower phase transformation temperatures, and high compressive toughness.

In another aspect, this invention includes a method of making an improved energy and ion conducting device. A stoichiometric nanoscale starting powder is reduced at a temperature between 500° C. and 1200° C. in a forming gas to yield non-stoichiometric nanopowders. The powders are pressed into discs, sintered, and coated with a cermet paste comprising equal parts silver and a stoichiometric nanoscale form of the starting powder. Platinum leads are then attached to the cermet paste. Preferably, the cermet paste comprises silver and a non-stoichiometric version of the starting powder. The starting powder may be yttria-stabilized cubic zirconia, other metal oxides, a perovskite material, or another group IV oxide. This invention also includes the improved energy and ion conducting device produced by this method. In addition, it includes an ion and energy conducting device wherein the ion conductor is produced from nanostructured beta alumina, NASICON, lithium nitride, LISICON, silver iodide, $Rb_4Cu_{16}I_7Cl_{13}$, a polymer, or a perovskite.

In another aspect, this invention includes an improved dopant for semiconductor materials where the dopant comprises a non-stoichiometric nanocrystalline powder. The grain size of the non-stoichiometric nanocrystalline powder may be less than 80 nm, preferably 40 nm, and more preferably 10 nm. The non-stoichiometric nanocrystalline powder may include one or more materials selected from the group comprising $Ta_{2/3}O_{0.9}$, $Nb_{2/5}O_{0.74}$, $NiO_{0.98}$, $Mn_{1/2}O_{0.9}$, $Bi_{2/3}O_{0.45}$, $Cu_{1.9}O$, $TiO_{1.1}$, $SiO_{1.55}$, and $V_{2/5}O_{0.0975}$.

Briefly stated, the present invention is directed to inks based on novel nanofillers that enhance a wide range of properties. In another aspect, the present invention is directed to methods for preparing nanocomposites that enable nanotechnology applications offering superior functional performance. In an example method, nanofillers and a substance having a polymer are mixed. Both low-loaded and highly-loaded nanocomposites are contemplated. Nanoscale coated and un-coated fillers may be used. Nanocomposite films may be coated on substrates.

In one aspect, the invention comprises a nanostructured filler, intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate.

The nanostructured filler may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

Another aspect of the invention comprises a method of producing a composite, comprising blending a nanoscale filler with a matrix to form a nanostructured composite. Either the nanostructured filler or the composite itself differs substantially in a desired material property from a micron-scale filler or composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility, and wear rate. The loading of the filler does not exceed 95 volume percent, and loadings of 80 volume percent or less are preferred.

The composite may be formed by mixing a precursor of the matrix material with the nanofiller, and then processing the precursor to form a desired matrix material. For example, the nanofiller may be mixed with a monomer, which is then polymerized to form a polymer matrix composite. In another embodiment, the nanofiller may be mixed with a matrix powder composition and compacted to form a solid composite. In yet another embodiment, the matrix composition may be dissolved in a solvent and mixed with the nanofiller, and then the solvent may be removed to form a solid composite. In still another embodiment, the matrix may be a liquid or have liquid like properties.

Yet another aspect of the invention is to prepare nanofillers for inks and dopants including pastes and slurries thereof. These pastes and slurries are then utilized to print nanoscale layers and structures.

Many nanofiller compositions are encompassed within the scope of the invention, including nanofillers comprising one or more elements selected from the group consisting of actinium, aluminum, arsenic, barium, beryllium, bismuth, cadmium, calcium, cerium, cesium, cobalt, copper, dysprosium, erbium, europium, gadolinium, gallium, gold, hafnium, hydrogen, indium, iridium, iron, lanthanum, lithium, magnesium, manganese, mendelevium, mercury, molybdenum, neodymium, neptunium, nickel, niobium, osmium, palladium, platinum, potassium, praseodymium, promethium, protactinium, rhenium, rubidium, scandium, silver, sodium, strontium, tantalum, terbium, thallium, thorium, tin, titanium, tungsten, vanadium, ytterbium, yttrium, zinc, and zirconium.

"Domain size" as that term is used herein, refers to the minimum dimension of a particular material morphology. In the case of powders, the domain size is the grain size. In the case of whiskers and fibers, the domain size is the diameter. In the case of plates and films, the domain size is the thickness.

As used herein, a "nanostructured powder" is one having a domain size of less than 100 nm, or alternatively, having a domain size sufficiently small that a selected material property is substantially different from that of a micron-scale powder, due to size confinement effects (e.g., the property may differ by 20% or more from the analogous property of the micron-scale material). Nanostructured powders often advantageously have sizes as small as 50 nm, 30 nm, or even smaller. Nanostructured powders may also be referred to as "nanopowders" or "nanofillers." A nanostructured composite is a composite comprising a nanostructured phase dispersed in a matrix.

As it is used herein, the term "agglomerated" describes a powder in which at least some individual particles of the powder adhere to neighboring particles, primarily by electrostatic forces, and "aggregated" describes a powder in which at least some individual particles are chemically bonded to neighboring particles.

BRIEF DESCRIPTION OF THE DRAWINGS

The invention is described with reference to the several figures of the drawing, in which.

DETAILED DESCRIPTION OF THE PREFERRED EMBODIMENTS

Figure 1:
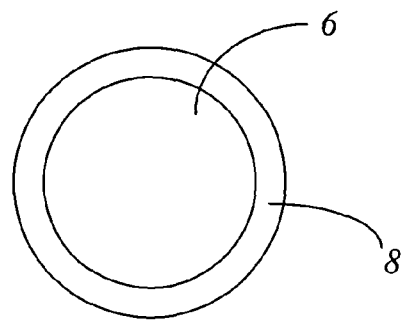
FIG. 1 is a diagram of a nanostructured filler coated with a polymer.

Non-stoichiometric substances in this invention are envisioned as substances that bridge between the artificial classification of substances—i.e. metals, alloys, oxides, carbides, nitrides, borides, sulfides, chalcogenides, silicides, etc. For example, while tin (Sn) is a metal, tin oxide ($SnO_2$) is an oxide ceramic. Non-stoichiometric tin oxide is then a form of a substance that transitions the properties of metallic tin to ceramic tin oxide. For example, non-stoichiometric tin oxides can be prepared with composition such as $SnO_{0.04}$, $SnO_{0.14}$, $SnO_{0.24}$, $SnO_{0.34}$, $SnO_{0.44}$, $SnO_{0.54}$, $SnO_{0.64}$, $SnO_{0.74}$, $SnO_{0.84}$, and $SnO_{0.94}$. The physical, thermal, chemical, and other properties of tin and tin oxide are very different, and the properties of non-stoichiometric tin oxide are anticipated to be very different and unique when compared with both metallic tin and ceramic tin oxide. The presence of vacancies in $SnO_x$ is anticipated to lead to higher conductivities, novel catalytic properties, novel structural properties, novel magnetic properties, faster sintering, and other desirable commercial performance. A preferred embodiment is to use a submicron non-stoichiometric form. A more preferred embodiment is to use a nanoscale non-stoichiometric form. It is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

Another illustration, without limiting the scope of this invention, is the non-metal boron and the ceramic boron nitride. In stoichiometric form, boron is B, and the ceramic boron nitride is BN. These two materials have very different molecular orbitals and different physical, thermal, chemical, optical, catalytic, structural, and other properties. Additionally, it is easier to process boron than boron nitride. Illustrative but not limiting forms of non-stoichiometric boron nitride include $BN_{0.025}$, $BN_{0.125}$, $BN_{0.225}$, $BN_{0.325}$, $BN_{0.425}$, $BN_{0.525}$, $BN_{0.625}$, $BN_{0.725}$, $BN_{0.825}$, $BN_{0.925}$. It is anticipated that nanoscale forms of these non-stoichiometric $BN_x$ will yield novel electrical and electronic properties, novel catalytic properties, novel structural properties, novel magnetic properties, faster sintering, and other desirable commercial performance. Once again, a preferred embodiment is to use a submicron non-stoichiometric form. A more preferred embodiment is to use a nanoscale non-stoichiometric form. Once again, it is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

Yet another illustration, without limiting the scope of this invention, is metallic titanium and the ceramic titanium carbide. In stoichiometric form, metallic titanium is Ti, and ceramic titanium carbide is TiC. These two materials have very different molecular orbitals and different physical, thermal, chemical, optical, catalytic, structural, and other properties. It is easier to process metals than ceramics, and the ductilities of metals are very different than those of ceramics. Illustrative but not limiting forms of non-stoichiometric titanium carbide include $TiC_{0.05}$, $TiC_{0.15}$, $TiC_{0.25}$, $TiC_{0.35}$, $TiC_{0.45}$, $TiC_{0.55}$, $TiC_{0.65}$, $TiC_{0.75}$, $TiC_{0.85}$, $TiC_{0.95}$. It is anticipated that nanoscale forms of nonstoichiometric $TiC_x$ will yield novel electrical and electronic properties, novel catalytic properties, novel structural properties, novel magnetic properties, faster sintering, and other desirable commercial performance. Once again, a preferred embodiment is to use a submicron non-stoichiometric form. A more preferred embodiment is to use a nanoscale non-stoichiometric form. Once again, it is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

A further illustration, without limiting the scope of this invention, is the nickel iron alloy and the ceramic nickel ferrite. In stoichiometric form, nickel iron alloy is NiFe, and ceramic nickel ferrite is $NiFe_2O_4$. These two materials have very different molecular orbitals and different physical, thermal, chemical, optical, catalytic, structural, and other properties. It is easier to process alloys than ceramics, and the ductilities of alloys are very different than those of ceramics. Illustrative but not limiting forms of non-stoichiometric nickel ferrite include $NiFe_2O_{3.91}$, $NiFe_2O_{3.71}$, $NiFe_2O_{3.51}$, $NiFe_2O_{3.31}$, $NiFe_2O_{3.11}$, $NiFe_2O_{2.91}$, $NiFe_2O_{2.71}$, $NiFe_2O_{2.51}$, $NiFe_2O_{2.31}$, $NiFe_2O_{2.11}$, $NiFe_2O_{1.91}$, $NiFe_2O_{1.71}$, $NiFe_2O_{1.51}$, $NiFe_2O_{1.31}$, $NiFe_2O_{1.11}$, $NiFe_2O_{0.91}$, $NiFe_2O_{0.71}$, $NiFe_2O_{0.51}$, $NiFe_2O_{0.31}$, $NiFe_2O_{0.11}$, $NiFe_{1.8}O_4$, $NiFe_{0.8}O_4$, $Ni_{0.9}Fe_2O_{3.9}$, $Ni_{0.9}Fe_2O_4$, and $Ni_{0.4}Fe_2O_4$. It is anticipated that nanoscale forms of non-stoichiometric nickel ferrite will yield novel electrical and electronic properties, novel catalytic properties, novel structural properties, novel magnetic properties, faster sintering, and other desirable commercial performance. Once again, a preferred embodiment is to use a submicron non-stoichiometric form. A more preferred embodiment is to use a nanoscale non-stoichiometric form. Once again, it is important to note that the non-stoichiometric form can be converted to a stoichiometric form if and when desired. Thus, the beneficial properties of non-stoichiometric forms can be utilized in some applications during processing, while leaving the flexibility for use of either a stoichiometric or a non-stoichiometric form in the final product.

Nanostructured materials have small grain sizes and high interfacial areas. Nanostructured materials can be prepared by methods such as those taught by us in commonly assigned U.S. Pat. No. 5,788,738 and others such as U.S. Pat. Nos. 5,486,675, 5,447,708, 5,407,458, 5,219,804, 5,194,128, 5,064,464, all of which are incorporated herein by reference. Relatively high surface area and small grain size makes nanopowders commercially suitable for processing into non-stoichiometric forms.

The material compositions to be used in the presently claimed invention are nanostructured non-stoichiometric substances, i.e. materials whose domain size have been engineered to sub-micron levels, preferably to nanoscale levels (<100 nm) where domain confinement effects become observable, modifying the properties of the materials. The scope of this invention excludes non-stoichiometry that results from thermodynamically favored defect structure.

Nanostructured materials (nanomaterials) are a novel class of materials whose distinguishing feature is that their average grain size or other domain size is within a size range where a variety of confinement effects dramatically change the properties of the material. A property will be altered when the entity or mechanism responsible for that property is confined within a space smaller than the critical length associated with that entity or mechanism. Some illustrations of such properties include but are not limited to electrical conductivity, dielectric constant, dielectric strength, dielectric loss, polarization, permittivity, critical current, superconductivity, piezoelectricity, mean free path, curie temperature, critical magnetic field, permeability, coercive force, magnetostriction, magnetoresistance, hall coefficient, BHmax, critical temperature, melting point, boiling point, sublimation point, phase transformation conditions, vapor pressure, anisotropy, adhesion, density, hardness, ductility, elasticity, porosity, strength, toughness, surface roughness, coefficient of thermal expansion, thermal conductivity, specific heat, latent heat, refractive index, absorptivity, emissivity, dispersivity, scattering, polarization, acidity, basicity, catalysis, reactivity, energy density, activation energy, free energy, entropy, frequency factor, environmental benignness, bioactivity, biocompatibility, and thermal and pressure coefficients of properties. The importance of nanostructured materials to this invention can be illustrated by considering the example of the mean free path of electrons, which is a key determinant of a material's resistivity. The mean free path in conventional materials and resistivity are related by:

$$\rho = mv_E/nq^2\lambda$$

where,
$\rho$: resistivity
m: mass of electron
$v_E$: Fermi energy
n: number of free electrons per unit volume in material
q: charge of electron
$\lambda$: mean free path of electron This equation assumes that the resistivity in the material is determined in part by the mean free path of electrons and that the electrons have a free path in the bulk. In nanostructured materials, the domain size is confined to dimensions less than the mean free path and the electron meets the interface of the domain before it transverses a path equal to the mean free path. Thus, if the material's domain size is confined to a size less than the mean free path, this equation is no longer valid. In a simplistic model, one could replace $\lambda$ with the domain size, but that replacement ignores the fact that confinement can also affect "n" and other fundamental properties. This insight suggests that unusual properties may be expected from devices prepared from materials with a domain size less than the mean free path of electrons.

While the above argument is discussed in light of mean free path, it is important to note that the domain confinement effect can be observed even when the domain size is somewhat larger than the mean free path because: (a) "mean" free path is a statistical number reflecting a mean of path lengths statistically observed in a given material, and (b) in very finely divided materials, the interface volume is significant and all the free electrons do not see the same space; electrons closer to the interface interact differently than those localized in the center of the domain.

The significance of using nanostructured materials can be further appreciated if the conductivity of semiconducting oxides is considered as shown in the equation for conductivity from hopping mechanism:

$$\sigma = P_a P_b 2e^2/ckTv[\exp(q/kT)]$$

where,
$\sigma$: conductivity
$P_a$, $P_b$: probabilities that neighboring sites are occupied by desirable cations e: electronic charge
n: frequency factor
k: Boltzmann's constant
T: temperature
q: activation energy
c: unit cell dimension
v: hopping velocity The frequency factor and activation energy are a strong function of the microstructure confinement and non-stoichiometry; therefore, the conductivity of the same material can be very different in nanostructured non-stoichiometric form when compared with naturally occurring bulk crystal form of the substance.

As the phrase is used herein, "nanostructured materials" are considered to be materials with a domain size less than 5 times the mean free path of electrons in the given material, preferably less than the mean free path of electrons. Alternatively, the domain size may be less than 500 nanometers, and preferably less than 100 nanometers. Nanostructured materials also include substances with a mean domain size less than or equal to the domain size below which the substance exhibits 10% or more change in at least one property of the said substance when the domain size is changed by a factor of 2, everything else remaining the same. Furthermore, the term nanostructured materials incorporates zero dimensional, one dimensional, two dimensional, and three dimensional materials.

Nanopowders in this invention are nanostructured materials wherein the domain size is the powder's grain size. For the scope of the invention, the term nanopowders includes powders with an aspect ratio different than one, and more specifically powders that satisfy the relation: $10^0 <$ aspect ratio $< 10^6$.

Submicron materials in this disclosure are materials with mean grain size less than 1 micrometer.

Non-stoichiometric materials are metastable materials, which have a composition that is different than that required for stoichiometric bonding between two or more elements. For example, stoichiometric titania can be represented as $TiO_2$ while non-stoichiometric titania can be represented as $TiO_{2-x}$ ($TiO_{1.8}$ and $TiO_{1.3}$ would be two specific examples of non-stoichiometric titania). Stoichiometric bonding between two or more elements indicates that charge balance is achieved among the said elements. In general, a stoichiometric material is given by:

$$M_n Z_p$$

where, Z can be any element from the p, d, and f groups of the periodic table (illustrations include: C, O, N, B, S, H, Se, Te, In, Sb, Al, Ni, F, P, Cl, Br, I, Si, and Ge). M can be any element that can lower its free energy by chemically bonding with Z (illustrations include: Ti, Mn, Fe, Ni, Zn, Cu, Sr, Y, Zr, Ta, W, Sc, V, Co, In, Li, Hf, Nb, Mo, Sn, Sb, Al, Ce, Pr, Be, Np, Pa, Gd, Dy, Os, Pt, Pd, Ag, Eu, Er, Yb, Ba, Ga, Cs, Na, K, Mg, Pm, Pr, Ni, Bi, Tl, Ir, Rb, Ca, La, Ac, Re, Hg, Cd, As, Th, Nd, Th, Md, and Au), where n and p, integers for stoichiometric bonding between M and Z, are greater than or equal to 1.

A non-stoichiometric form of the same material may then be given by:

$$M_{nx} Z_{py}$$

where $0<x<n$ and $0<y<p$.

An alternative representation of a non-stoichiometric material is $M_{n/p} Z_{1-x}$, where $0<x<1$. In this invention, the preferred range includes $0.01<x<0.99$, preferably $0.02<x<0.98$, and more preferably $0.05<x<0.95$.

Empirical methods may also be used to determine whether a material is non-stoichiometric. Some embodiments of such methods are as follows:

1. Heat a stoichiometric form of the material and the material being evaluated for non-stoichiometry separately in a reactive atmosphere (e.g., oxygen, if oxygen non-stoichiometry is being ascertained) to 0.5 times the melting point of the material; monitor the weight change per unit sample weight. The material being evaluated is non-stoichiometric if its weight change per unit sample weight is greater than either 1% of the weight of the sample or 25% of the weight change in the sample of stoichiometric form.

2. Alternatively, perform a quantitative elemental analysis on the material; if the relative ratio of the elements yields an "x" that is not an integer (and the relative ratio deviates by more than 1%, preferably more than 2% and more preferably by more than 5%), the material is non-stoichiometric.

3. Alternatively, measure the properties of the material in the ideal stoichiometric form and compare this with the substance being evaluated for non-stoichiometry; if any property of the material, or the temperature coefficient of any property varies by more than 10% between the two substances, everything else remaining the same, the substance being evaluated is non-stoichiometric.

These empirical methods will not work universally and may give misleading results because some materials decompose with heating, and analytical techniques are prone to statistical errors. These empirical methods should not be considered limiting and other methods of establishing "x" fall within the scope of the invention.

In the $M_{n-x} Z_{p-y}$ representation discussed above, non-stoichiometric materials may have more than one "M," more than one "Z," or both. In this case, the representation can be $\Pi_{I_j}(M_{I,ni-xi} Z_{j,pj,yj})$, where $\Pi_{I_j}$ represents a multiplicity in i and j. A material is then non-stoichiometric if the relative ratio of any M or any Z or any combination is different by more than 2.5% than what is needed for theoretical bonding between the said elements. Some illustrations of this, without limiting the scope of the invention, would be non-stoichiometric compositions such as $BaTiO_{3-x}$, $Ba_{1-x}TiO_3$, $NiFe_2O_{3-x}$, $Ni_{1-x}Fe_2O_3$, $NiFe_2O_3N_{1-x}$, $PbZrTiO_{3-x}$, $TiCN_{1-x}$, and $TiC_{1-x}N$. It is also important to note that, for the scope of this invention, non-stoichiometric substances include substances produced when one or more of Z and/or M in $\Pi_{I_j}(M_{I,ni-xi} Z_{j,pj,yj})$ is replaced partially or completely with additional elements, i.e., $Z_s$ or $M_s$. An example of this would be stoichiometric $MnFe_2O_4$, which, after processing, becomes $MnFe_2O_{3.5}N_{0.1}$ or $MnFe_2O_{3.1}B_{0.3}$. Another example of this is stoichiometric $TiB_2$ which after processing becomes $TiB_{1.5}N_{0.3}$ or $TiB_{1.1}C_{0.2}$.

It is important to note that all naturally produced and artificially produced materials have defects because defects are thermodynamically favored. Such thermodynamically favored defects can lead to small amounts of inherent non-stoichiometry in substances. The presently claimed non-stoichiometric materials differ from such naturally produced and artificially produced substances in the following:

This invention excludes from its scope the non-stoichiometry that naturally results from the randomly occurring thermodynamic defects in a bulk crystal of the theoretical stoichiometry which are typically on the order of a few hundred parts per million. Preferred levels of non-stoichiometry according to the invention are those which significantly exceed equilibrium levels. Alternatively, the preferred ranges include $0.01<x<0.99$, preferably $0.02<x<0.98$, and more preferably $0.05<x<0.95$.

This invention teaches the methods for engineering unusual non-stoichiometric compositions, and provides motivation to harness their unusual properties. The invention stabilizes and makes non-stoichiometry commercially attractive by engineering nanostructure in the non-stoichiometric material. It should be noted that nanostructured non-stoichiometric substances are anticipated to have interfacial stresses that play an important role in determining the unique properties and unusual thermodynamic nature of these substances, thereby yielding materials with unprecedented compositions of matter and performance.

In the presently claimed invention, the scope of the invention includes nanostructured materials with a domain size less than 5 times the mean free path of electrons in the given material, preferably less than the mean free path of electrons. In the event that it is difficult to theoretically compute the mean free path of the non-stoichiometric material under consideration, it is recommended that the domain size be less than 500 nanometers, preferably less than 100 nanometers. If it is difficult to measure the grain size or the grain size changes during the production or use of the device, the scope of the invention includes non-stoichiometric materials with a domain size that exhibit 10% or more change in at least one property of the said substance when the domain size is changed by a factor of 2, everything else remaining same.

A very wide range of material properties and product performance can be engineered by the practice of the invention. For example, unusual or improved electrical, electronic, magnetic, optical, electrochemical, chemical, catalytic, thermal, structural, biomedical, surface properties, and combinations thereof can be obtained or varied over a wider range using nanostructured non-stoichiometric substances than is possible using prior art stoichiometric substances. Such benefits can motivate use of these materials in pellet or film type or multilayer type devices and products.

Nanostructured non-stoichiometric substances can be used as fillers to lower or raise the effective resistivity, effective permittivity, and effective permeability of a polymer or ceramic matrix. While these effects are present at lower loadings, they are expected to be most pronounced for filler loadings at or above the percolation limit of the filler in the matrix (i.e. at loadings sufficiently high that electrical continuity exists between the filler particles). Other electrical properties which could potentially be engineered include breakdown voltage, skin depth, curie temperature, temperature coefficient of electrical property, voltage coefficient of electrical property, dissipation factor, work function, band gap, electromagnetic shielding effectiveness and degree of radiation hardness. Nanostructured non-stoichiometric fillers can also be used to engineer magnetic properties such as the coercivity, BH product, hysteresis, and shape of the BH curve of a matrix. Even when non-stoichiometric substances are used in monolithic form, these unique electrical, magnetic, and electronic properties hold significant commercial interest.

Other important characteristics of an optical material are its refractive index and transmission and reflection characteristics. Nanostructured non-stoichiometric substances can be used to produce composites with refractive indices engineered for a particular application. Gradient lenses produced from nanostructured non-stoichiometric composites are anticipated to reduce or eliminate the need for polishing lenses. The use of nanostructured non-stoichiometric substances are anticipated to also help filter specific wavelengths. Furthermore, an expected advantage of nanostructured non-stoichiometric substances in optical applications is their enhanced transparency because the domain size of nanostructured fillers ranges from about the same as to more than an order of magnitude less than visible wavelengths of light. Photonic applications where specific wavelengths of light are processed are anticipated to utilize the unique optical properties of non-stoichiometric substances.

The high surface area and small grain size of non-stoichiometric substances and their composites make them excellent candidates for chemical and electrochemical applications. When used to form electrodes for electrochemical devices, these materials are expected to significantly improve performance, for example, by increasing power density in batteries and reducing minimum operating temperatures for sensors. Nanostructured non-stoichiometric substances are also expected to modify the chemical properties of composites. These unique non-stoichiometric substances are anticipated to be catalytically more active and to provide more interface area for interacting with diffusive species. They are anticipated to provide the materials needed in our commonly assigned U.S. patent application Ser. No. 09/165,439 on a method and process for transforming chemical species which utilizes electromagnetic fields, and which is incorporated by reference herein. Such substances are anticipated to also modify chemical stability and mobility of diffusing gases. Furthermore, nanostructured non-stoichiometric substances are anticipated to enhance the chemical properties of propellants and fuels or safety during storage and transportation or both.

Many nanostructured non-stoichiometric substances have a domain size comparable to the typical mean free path of phonons at moderate temperatures. These non-stoichiometric substances are anticipated to have dramatic effects on the thermal conductivity and thermal shock resistance of matrices and products into which they are incorporated. Potential applications include fluids used for heat transfer.

Nanostructured non-stoichiometric substances-which may be utilized in coated and uncoated form-and composites derived thereof are also expected to have significant value in biomedical applications for both humans and animals. For example, the small size of nanostructured non-stoichiometric substances will make them readily transportable through pores and capillaries. This suggests that the non-stoichiometric substances will be of use in developing novel time-release drugs and methods of administration and delivery of drugs, markers, and medical materials. A polymer coating can be utilized either to make water-insoluble fillers into a form that is water soluble, or to make water-soluble fillers into a form that is water insoluble. A polymer coating on the filler may also be utilized as a means to time drug-release from a nanoparticle. A polymer coating may further be used to enable selective filtering, transfer, capture, and removal of species and molecules from blood into the nanoparticle.

The invention can be used to prepare propellants and fuels that are safer to store, transport, process, and use. The non-stoichiometry can also provide increased energy density or oxidant or both.

The invention can be used to produce superior or more affordable catalysts for the synthesis of currently used and novel organic compounds, inorganic compounds, organometallic compounds, pharmaceuticals, polymers, petrochemicals, reagents, metallurgical products, and combinations thereof. The invention can also be used to produce superior or more affordable catalysts for environmental and other applications that currently or in the future can benefit from catalysis. Similarly, the invention can be used to produce superior or more affordable phosphors for monochromatic and color display applications.

A nanoparticulate non-stoichiometric filler for biomedical operations might be a carrier or support for a drug of interest, participate in the drug's functioning, or might even be the drug itself. Possible administration routes include oral, topical, and injection routes. Nanoparticulates and nanocomposites are anticipated to also have utility as markers or as carriers for markers. Their unique properties, including high mobility and unusual physical properties, make them particularly well-adapted for such tasks.

In some examples of biomedical functions, magnetic non-stoichiometric nanoparticles such as ferrites may be utilized to carry drugs to a region of interest, where the particles may then be concentrated using a magnetic field. Photocatalytic non-stoichiometric nanoparticles can be utilized to carry drugs to a region of interest and then photoactivated. Thermally sensitive non-stoichiometric nanoparticles can similarly be utilized to transport drugs or markers or species of interest and then thermally activated in the region of interest. Radioactive non-stoichiometric nanoparticulate fillers are anticipated to have utility for chemotherapy. Nanoparticles suitably doped with genetic, cultured, or other biologically active materials may be utilized in a similar manner to deliver therapy in target areas. Nanocomposite particles may be used to assist in concentrating the particle and then providing therapeutic action. To illustrate, magnetic and photocatalytic nanoparticles may be formed into a composite, administered to a patient, concentrated in area of interest using a magnetic field, and finally activated using photons directed to the concentrated particles. As markers, coated or uncoated non-stoichiometric nanoparticulate fillers may be used for diagnosis of medical conditions. For example, fillers may be concentrated in a region of the body where they may be viewed by magnetic resonance imaging or other techniques. In all of these applications, the possibility exists that nanoparticulates can be released into the body in a controlled fashion over a long time period, by implanting a nanocomposite material having a bioabsorbable matrix, which slowly dissolves in the body and releases its embedded filler.

Other benefits disclosed in co-owned U.S. Pat. No. 6,228,904 on nanostructured fillers, and which is incorporated by reference herein and recited below, are applicable to the non-stoichiometric materials of the present invention.

Prior art filler materials for polymeric composites are usually powders with an average dimension in the range of 10-100 μm. Thus, each filler particle typically has on the order of $10^{15}$-$10^{18}$ atoms. In contrast the typical polymer chain has on the order of $10^3$-$10^9$ atoms. While the art of precision manufacturing of polymers at molecular levels is well-developed, the knowledge of precision manufacturing of filler materials at molecular levels has remained largely unexplored.

The number of atoms in the filler particles of the invention (hereinafter called "nanostructured filler" or "nanofiller") is on the order of or significantly less than the number of atoms in the polymer molecules, e.g., $10^2$-$10^{10}$. Thus, the filler particles are comparable in size or smaller than the polymer molecules, and therefore can be dispersed with orders of magnitude higher number density. Further, the fillers may have a dimension less than or equal to the critical domain sizes that determine the characteristic properties of the bulk composition; thus, the fillers may have significantly different physical properties from larger particles of the same composition. This in turn may yield markedly different properties in composites using nanofillers as compared to the typical properties of conventional polymer composites.

These nanostructured filler materials may also have utility in the manufacture of other types of composites, such as ceramic- or metal-matrix composites. Again, the changes in the physical properties of the filler particles due to their increased surface area and constrained domain sizes can yield changes in the achievable properties of composites.

The nanofillers of the invention can be inorganic, organic, or metallic, and may be in the form of powders, whiskers, fibers, plates or films. The fillers represent an additive to the overall composite composition, and may be used at loadings of up to 95% by volume. The fillers may have connectivity in 0, 1, 2, or 3 dimensions. Fillers may be produced by a variety of methods, such as those described in U.S. Pat. Nos. 5,486,675; 5,447,708; 5,407,458; 5,219,804; 5,194,128; and 5,064,464. Particularly preferred methods of making nanostructured fillers are described in U.S. patent application Ser. No. 09/046,465, by Bickmore, et al., filed Mar. 23, 1998, now U.S. Pat. No. 5,984,997 and Ser. No. 08/706,819, by Pirzada, et al., filed Sep. 3, 1996, now U.S. Pat. No. 5,851,507 both of which are incorporated herein by reference.

A method of making nanostructured fillers is described in commonly owned U.S. patent application Ser. No. 09/046,465, by Bickmore, et al., filed Mar. 23, 1998, now U.S. Pat. No. 5,984,997 which is herewith recited. For example, if a doped complex of composition:

$$d_1-M_1M_2X$$

is desired, then according to the invention, one should prepare solutions or suspensions of dopant $d_1$, metals $M_1$ and $M_2$, and anion X, where $M_1$ and $M_2$ are selected from the s, p, f, and d groups of the periodic table, and X is selected from the p group of the periodic table. Solutions or suspensions may be prepared, for example, by mixing solutions containing each of the constituent elements of the desired powder. Elements dopant $d_1$, metals $M_1$ and $M_2$ are selected from the group consisting of the s group, p group, d group, or f group of the periodic table, and X is selected from the group consisting of carbon, nitrogen, oxygen, boron, phosphorus, sulfur, chalcogens, and halogens.

It will be understood by those skilled in the art that powders comprising larger numbers of dopants, metals, and anions can also be produced by the same methods. In particular, polymetallic materials comprising at least three metals and at least one anion can be produced. These materials are useful in the manufacture of capacitors, inductors, varistors, resistors, piezo-devices, thermistors, thermoelectric devices, filters, connectors, magnets, ion-conducting devices, sensors, fuel cells, catalysts, optics, photonic devices, lasers, tooling bits, armor, superconductors, inks, and pigments, for example. Prior art polymetallic powders are limited to sizes in excess of 300 nm, and mostly to sizes in excess of 1 micrometer. By the methods of the invention, solid or porous polymetallic nanopowders can be made, with sizes less than 250 nm, and preferably less than 100 nm. Furthermore, by the methods of the invention, nano-whiskers and nano-rods can be produced with aspect ratios of 25 or less, having a minimum dimension of less than 250 nm, and preferably less than 100 nm. At this scale, size confinement effects can come into play for many polymetallic powders.

While this invention does not limit itself to a specific cation or anion, it is desirable to use anions and cations that are either part of the final product or completely volatile. The final products are not limited to ionic materials, and include covalent and mixed ionic-covalent materials such as carbides, borides, nitrides, sulfides, oxycarbides, oxynitrides, oxyborides and oxysulfides. Illustrative formulations, but not exhaustive, then are nitrate, nitrites, nitrites, nitrides, carbonates, bicarbonates, hydroxides, cyanos, organometallics, carboxylates, amines, and amides.

In one aspect of commonly owned U.S. patent application Ser. No. 09/046,465, by Bickmore, et al., filed Mar. 23, 1998, now U.S. Pat. No. 5,984,997 which is herewith recited, the invention comprises a method of continuously producing fine powders of complex inorganic compositions, including, but not limited to, carbides, nitrides, oxides, chalcogenides, halides, phosphides, borides, and combinations thereof by combustion of emulsions. By varying the characteristics of the initial emulsion, the size, shape, surface area, morphology, surface characteristics, surface composition, distribution, and degree of agglomeration of the final powder may be controlled. And, in conjunction with varying combustion conditions, the product chemistry may be varied to obtain non-stoichiometric, reduced oxide, or mixed anion materials. Examples of this embodiment include the use of non-stoichiometric flames or reducing gases such as hydrogen, forming gas, or ammonia. It is an advantage of these aspects of the invention that the method can use low cost, safe, readily available and environmentally benign precursors to produce fine powders. In a preferred embodiment, the method ensures high yield and high selectivity, including harvesting 95% or more of the fine powder produced. In another embodiment, the method prevents the damage of the fine powders during and after their synthesis.

In another aspect, the invention includes multimetallic powders having a median particle size of less than 5 micron and a standard deviation of particle size of less than 100 nm. In preferred embodiments, the median particle size is less than 100 nm and the standard deviation of particle size is less than 25 nm, and in further preferred embodiments, the median particle size is less than 30 nm and the standard deviation of particle size is less than 10 nm. The multimetallic powders include at least two elements selected from the s group, p group, d group, and f group of the periodic table (e.g., aluminum, antimony, barium, bismuth, boron, bromine, cadmium, calcium, carbon, cerium, cesium, chlorine, chromium, cobalt, copper, dysprosium, erbium, europium, gadolinium, gallium, germanium, gold, hafnium, holmium, indium, iodine, iridium, iron, lanthanum, lead, lithium, lutetium, magnesium, manganese, molybdenum, neodymium, nickel, niobium, nitrogen, osmium, oxygen, palladium, phosphorus, platinum, praseodymium, potassium, rhenium, rhodium, rubidium, samarium, scandium, silicon, silver, sodium, strontium, sulfur, tantalum, terbium, thulium, tin, titanium, tungsten, vanadium, ytterbium, yttrium, zinc, and zirconium), and may include three or more such elements. The powders may be unagglomerated and/or unaggregated. The multimetallic powders may also comprise nanowhiskers and/or nanorods, with aspect ratios in a range of 1-25.

The term "nanopowder" describes a powder whose mean diameter is so small that its physical properties are substantially affected by size related confinement effects. Nanopowders usually have a mean diameter less than or equal to 250 nm, and preferably have a mean diameter less than or equal to 100 nm. More preferably, nanopowders may have a mean diameter less than 50 nm.

The term "aspect ratio" refers to the ratio of the maximum to the minimum dimension of a particle. The term "whisker" refers to any elongated particle (e.g., a particle having an aspect ratio greater than one, and preferably at least two). Whiskers may be round or faceted, and may have varying diameters. "Rods" are substantially cylindrical whiskers. "Nanowhiskers" and "nanorods" refer to rods and whiskers whose smallest dimension is so small that their physical properties are substantially affected by size related confinement effects. Nanowhiskers and nanorods usually have a minimum dimension less than or equal to 250 nm, and preferably have a minimum dimension less than or equal to 100 nm. More preferably, these particles may have a minimum dimension less than 50 nm.

A distinctive feature of the invention described in commonly owned U.S. patent application Ser. No. 09/046,465, by Bickmore, et al., filed Mar. 23, 1998, now U.S. Pat. No. 5,984,997 which is herewith recited, is the use of emulsion as the vehicle for carrying fuels and metals. Once an emulsion formulation has been established, dopants and other metals can be readily added to the said emulsion to prepare and vary complex compositions. It will be understood by those skilled in the art that powders comprising larger numbers of dopants, metals, and anions can also be produced by the same methods. In particular, polymetallic materials comprising at least three metals and at least one anion can be produced. These materials are useful in the manufacture of capacitors, inductors, varistors, resistors, piezo-devices, thermistors, thermoelectric devices, filters, connectors, magnets, ion-conducting devices, sensors, fuel cells, catalysts, optics, photonic devices, lasers, tooling bits, armor, superconductors, inks, and pigments, for example. Prior art polymetallic powders are limited to sizes in excess of 300 nm, and mostly to sizes in excess of 1 micrometer. By the methods of the invention, solid or porous polymetallic nanopowders can be made, with sizes less than 250 nm, and preferably less than 100 nm. Furthermore, by the methods of the invention, nano-whiskers and nano-rods can be produced with aspect ratios of 25 or less, having a minimum dimension of less than 250 nm, and preferably less than 100 nm. At this scale, size confinement effects can come into play for many polymetallic powders.

The solutions or suspensions of the invention can be aqueous based or organic based. While this invention does not limit itself to a specific cation or anion, it is desirable to use anions and cations that are either part of the final product or completely volatile. The final products are not limited to ionic materials, and include covalent and mixed ionic-covalent materials such as carbides, borides, nitrides, sulfides, oxycarbides, oxynitrides, oxyborides and oxysulfides. Illustrative formulations, but not exhaustive, then are nitrate, nitrites, nitrites, nitrides, carbonates, bicarbonates, hydroxides, cyanos, organometallics, carboxylates, amines, and amides. Once the individual solutions or suspensions are available, an emulsion is prepared from the solution or suspensions.

A distinctive feature of the invention is the use of emulsion as the vehicle for carrying fuels and metals. Once an emulsion formulation has been established, dopants and other metals can be readily added to the said emulsion to prepare and vary complex compositions. The approach here is that the emulsion formulation(s) and dopants can be stored separately and then mixed at will to achieve an application-specific complex composition. To vary the final composition, the proportion of formulation(s) and dopants can be changed. To illustrate, if two separate emulsion formulations are available for preparing $M_1O$ and $M_2O$, then the composition $(M_1)_{0.1}(M_2)_{0.9}O$ can be prepared by mixing the two formulations in 10:90 ratio respectively; on the other hand, if the composition $(M_1)_{0.9}(M_2)_{0.1}O$ is desired, it can be prepared by mixing the two formulations in 90:10 ratio respectively. One or more dopants can also be added as desired. For more complex formulations, one can mix different emulsions and dopants. An advantage of the invention is that a wide range of complex nanoscale powder compositions can be prepared from a small set of ingredients, that is, emulsion formulation(s) and dopant solutions. Another advantage is that the cost of producing specific compositions can be lowered from economies possible in preparing common ingredients in bulk. Yet another advantage is that emulsions can be prepared from very low-cost, readily available precursors. As will be apparent to those skilled in the art, it is important to ensure that the emulsions being mixed are compatible. It will also be apparent that many emulsions can be prepared for the same metal—a fact that adds versatility to this invention.

The emulsion may be either polar-in-non-polar (water-in-oil) or non-polar-in-polar (oil-in-water) or of any other at least temporarily stable type, including polar-in-polar and non-polar-in-non-polar. Some representative stable emulsions are described, for example, in Kirk-Othmer, "Emulsions," Encyclopedia of Chemical Technology, Vol 9, Wiley-Interscience, New York, 1994, which along with the reference cited therein is herewith incorporated in entirety. While stable emulsions are preferred, metastable emulsions and temporarily stable emulsions are also within the scope of the invention. To practice the invention, metastable emulsions and temporarily stable emulsions must be stable for a time at least equal to or greater than the time needed to transport and combust the emulsion.

According to the invention, at least one component of the emulsion acts as a fuel. The fuel component can be part of one of the solution phases or can be separately added to achieve combustibility. Emulsifying agents and dispersants may also be added to homogenize or stabilize the emulsion, to enhance combustion, or to achieve a combination of these characteristics.

The emulsions are pumped directly and atomized, or, alternatively, carried in a gas or a mix of gases that do not possess or do not contribute an element that is not desired in the final composition. Preferred carrier stream gases are nitrogen, air, oxygen, argon, helium, neon, and xenon. It is also within the scope of the invention to include in the carrier stream a reactant such as ammonia gas.

The emulsion is combusted using designs such as, but not limited to, those taught by Khavkin (Combustion System Design, PennWell Books, Tulsa Okla., 1996) and Fischer (Combustion Engineer's Handbook, G. Newnes Publisher, London, 1961), which are incorporated herein by reference. The combustion can be accomplished using a laminar or turbulent flame, a premixed or diffusion flame, a co-axial or impinging flame, a low-pressure or high-pressure flame, a sub-sonic or sonic or super-sonic flame, a pulsating or continuous flame, an externally applied electromagnetic field free or externally applied electromagnetic field influenced flame, a reducing or oxidizing flame, a lean or rich flame, a secondary gas doped or undoped flame, a secondary liquid doped or undoped flame, a secondary particulate doped or undoped flame, an adiabatic or non-adiabatic flame, a one-dimensional or two-dimensional or three-dimensional flame, an obstruction-free or obstructed flame, a closed or open flame, an externally heated or externally cooled flame, a pre-cooled or pre-heated flame, a one burner or multiple burner flame, or a combination of one or more of the above. Usually, combustion temperatures will be in excess of 600° C., a temperature at which diffusion kinetics will be sufficiently fast that a compositionally uniform powder will be produced. The emulsion can also be a feed to other processes of producing nanoscale powders. Examples include the powder-formation processes described in and commonly assigned U.S. patent application Ser. No. 08/707,341, "Boundary Layer Joule—Thompson Nozzle for Thermal Quenching of High Temperature Vapors," now U.S. Pat. No. 5,788,738 and Ser. No. 08/706,819, "Integrated Thermal Process and Apparatus for the Continuous Synthesis of Nanoscale Powders," now U.S. Pat. No. 5,851,507, both of which are incorporated herein.

A wide variety of nanofiller compositions are possible. Some exemplary compositions include metals (e.g., Cu, Ag, Ni, Fe, Al, Pd, and Ti), oxide ceramics (e.g., $TiO_2$, $TiO_{2-x}$, $BaFe_2O_4$, dielectric compositions, ferrites, and manganites), carbide ceramics (e.g., SiC, BC, TiC, WC, WCsub.1-x), nitride ceramics (e.g., $Si_3N_4$, TiN, VN, AlN, and $Mo_2N$), hydroxides (e.g., aluminum hydroxide, calcium hydroxide, and barium hydroxide), borides (e.g., $AlB_2$ and $TiB_2$), phosphides (e.g., NiP and VP), sulfides (e.g., molybdenum sulfide, titanium sulfide, and tungsten sulfide), silicides (e.g., $MoSi_2$), chalcogenides (e.g., $Bi_2Te_3$, $Bi_2Se_3$), and combinations of these.

The fillers are immediately mixed with a matrix material, which is preferably polymeric, buy may also be ceramic, metallic, or a combination of the above. The matrix may be chosen for properties such as ease of processability, low cost, environmental benignity, commercial availability, and compatibility with the desired filler. The fillers are preferably mixed homogeneously into the matrix, but may also be mixed heterogeneously if desired, for example to obtain a composite having a gradient of some property. Mixing techniques for incorporating powders into fluids and for mixing different powders are well known in the art, and include mechanical, thermal, electrical, magnetic, and chemical momentum transfer techniques, as well as combinations of the above.

The viscosity, surface tension, and density of a liquid matrix material can be varied for mixing purposes, the preferred values being those that favor ease of mixing and that reduce energy needed to mix without introducing any undesirable contamination. One method of mixing is to dissolve the matrix in a solvent which does not adversely affect the properties of the matrix or the filler and which can be easily removed and recovered. Another method is to melt the matrix, incorporate the filler, and cool the mixture to yield a solid composite with the desired properties. Yet another method is to synthesize the matrix in-situ with the filler present. For example, the nanofiller can be mixed with a liquid monomer, which can then be polymerized to form the composite. In this method, the filler may be used as a catalyst or co-catalyst for polymerization. The mixing may also be accomplished in the solid state, for example by mixing a powdered matrix composition with the filler, and then compacting the mixture to form a solid composite.

Mixing can be assisted using various secondary species such as dispersants, binders, modifiers, detergents, and additives. Secondary species may also be added to enhance one to more of the properties of the filler-matrix composite.

Mixing can also be assisted by pre-coating the nanofiller with a thin layer of the matrix composition or with a phase that is compatible with the matrix composition. Such a coated nanoparticle is illustrated in FIG. 1, which shows a spherical nanoparticle 6 and a coating 8. In one embodiment, when embedding nanofillers in a polymer matrix, it may be desirable to coat the filler particles with a related monomer. When mixing nanofillers into a ceramic matrix, pre-coating can be done by forming a ceramic layer around the nanoscale filler particle during or after the synthesis of the nanoscale filler, by methods such as partial oxidation, nitridation, carborization, or boronation. In these methods, the nanostructured filler is exposed to a small concentration of a precursor that reacts with the surface of the filler to form a ceramic coating. For example, a particle may be exposed to oxygen in order to create an oxide coating, to ammonia in order to create a nitride coating, to borane to create a boride coating, or to methane to create a carbide coating. It is important that the amount of precursor be small, to prevent thermal runaway and consequent conversion of the nanostructured filler into a ceramic particle.

In case of polymer matrix, the filler can be coated with a polymer or a monomer by numerous methods, for example, surface coating in-situ, spray drying a dispersion of filler and polymer solution, co-polymerization on the filler surface, and melt spinning followed by milling. A preferred method is surface coating in-situ. In this process, the filler is first suspended in demineralized water (or another solvent) and the suspension's pH is measured. The pH is then adjusted and stabilized with small addition of acid (e.g., acetic acid or dilute nitric acid) or base (e.g., ammonium hydroxide or dilute sodium hydroxide). The pH adjustment produces a charged state on the surface of the filler. Once a desired pH has been achieved, a coating material (for example, a polymer or other appropriate precursor) with opposite charge is introduced into the solvent. This step results in coupling of the coating material around the nanoscale filler and formation of a coating layer around the nanoscale filler. Once the layer has formed, the filler is removed from the solvent by drying, filtration, centrifugation, or any other method appropriate for solid-liquid separation. This technique of coating a filler with another material using surface charge can be used for a variety of organic and inorganic compositions.

When a solvent is used to apply a coating as in the in-situ surface coating method described above, the matrix may also be dissolved in the solvent before or during coating, and the final composite formed by removing the solvent.

A very wide range of material properties can be engineered by the practice of the invention. For example, electrical, magnetic, optical, electrochemical, chemical, thermal, biomedical, and tribological properties can be varied over a wider range than is possible using prior art micron-scale composites.

Nanostructured fillers can be used to lower or raise the effective resistivity, effective permittivity, and effective permeability of a polymer or ceramic matrix. While these effects are present at lower loadings, they are expected to be most pronounced for filler loadings at or above the percolation limit of the filler in the matrix (i.e., at loadings sufficiently high that electrical continuity exists between the filler particles). Other electrical properties which may be engineered include breakdown voltage, skin depth, curie temperature, temperature coefficient of electrical property, voltage coefficient of electrical property, dissipation factor, work function, band gap, electromagnetic shielding effectiveness and degree of radiation hardness. Nanostructured fillers can also be used to engineer magnetic properties such as the coercivity, B-H product, hysteresis, and shape of the B-H curve of a matrix.

An important characteristic of optical material is its refractive index and its transmission and reflective characteristics. Nanostructured fillers may be used to produce composites with refractive index engineered for a particular application. Gradient lenses may be produced using nanostructured materials. Gradient lenses produced from nanostructured composites may reduce or eliminate the need for polishing lenses. The use of nanostructured fillers may also help filter specific wavelengths. Furthermore, a key advantage of nanostructured fillers in optical applications is expected to be their enhanced transparency because the domain size of nanostructured fillers ranges from about the same as to more than an order of magnitude less than visible wavelengths of light.

The high surface area and small grain size of nanofilled composites make them excellent candidates for chemical and electrochemical applications. When used to form electrodes for electrochemical devices, these materials are expected to significantly improve performance, for example by increasing power density in batteries and reducing minimum operating temperatures for sensors. (An example of the latter effect can be found in and commonly assigned U.S. patent application Ser. No. 08/739,257, "Nanostructured Ion Conducting Solid Electrolytes," by Yadav, et al. now U.S. Pat. No. 5,905,000). Nanostructured fillers are also expected to modify the chemical properties of composites. These fillers are catalytically more active, and provide more interface area for interacting with diffusive species. Such fillers may, for example, modify chemical stability and mobility of diffusing gases. Furthermore, nanostructured fillers may enhance the chemical properties of propellants and fuels.

Many nanostructured fillers have a domain size comparable to the typical mean free path of phonons at moderate temperatures. It is thus anticipated that these fillers may have dramatic effects on the thermal conductivity and thermal shock resistance of matrices into which they are incorporated.

Nanostructured fillers—in coated and uncoated form—and nanofilled composites are also expected to have significant value in biomedical applications for both humans and animals. For example, the small size of nanostructured fillers may make them readily transportable through pores and capillaries. This suggests that the fillers may be of use in developing novel time-release drugs and methods of administration and delivery of drugs, markers, and medical materials. A polymer coating can be utilized either to make water-insoluble fillers into a form that is water soluble, or to make water-soluble fillers into a form that is water insoluble. A polymer coating on the filler may also be utilized as a means to time drug-release from a nanoparticle. A polymer coating may further be used to enable selective filtering, transfer, capture, and removal of species and molecules from blood into the nanoparticle.

A nanoparticulate filler for biomedical operations might be a carrier or support for a drug of interest, participate in the drug's functioning, or might even be the drug itself. Possible administration routes include oral, topical, and injection routes. Nanoparticulates and nanocomposites may also have utility as markers or as carriers for markers. Their unique properties, including high mobility and unusual physical properties, make them particularly well-adapted for such tasks.

In some examples of biomedical functions, magnetic nanoparticles such as ferrites may be utilized to carry drugs to a region of interest, where the particles may then be concentrated using a magnetic field. Photocatalytic nanoparticles can be utilized to carry drugs to region of interest and then photoactivated. Thermally sensitive nanoparticles can similarly be utilized to transport drugs or markers or species of interest and then thermally activated in the region of interest. Radioactive nanoparticulate fillers may have utility for chemotherapy. Nanoparticles suitably doped with genetic and culture material may be utilized in similar way to deliver therapy in target areas. Nanocomposites may be used to assist in concentrating the particle and then providing the therapeutic action. To illustrate, magnetic and photocatalytic nanoparticles may be formed into a composite, administered to a patient, concentrated in area of interest using magnetic field, and finally activated using photons in the concentrated area. As markers, nanoparticulate fillers—coated or uncoated—may be used for diagnosis of medical conditions. For example, fillers may be concentrated in a region of the body where they may be viewed by magnetic resonance imaging or other techniques. In all of these applications, the possibility exists that nanoparticulates can be released into the body in a controlled fashion over a long time period, by implanting a nanocomposite material having a bioabsorbable matrix, which slowly dissolves in the body and releases its embedded filler.

As implants, nanostructured fillers and composites are expected to lower wear rate and thereby enhance patient acceptance of surgical procedures. Nanostructured fillers may also be more desirable than micron-scale fillers, because the possibility exists that their domain size may be reduced to low enough levels that they can easily be removed by normal kidney action without the development of stones or other adverse side effects. While nanoparticulates may be removed naturally through kidney and other organs, they may also be filtered or removed externally through membranes or otherwise removed directly from blood or tissue. Carrier nanoparticulates may be reactivated externally through membranes and reused; for example, nutrient carriers may be removed from the bloodstream, reloaded with more nutrients, and returned to carry the nutrients to tissue. The reverse process may also be feasible, wherein carriers accumulate waste products in the body, which are removed externally, returning the carriers to the bloodstream to accumulate more waste products.

Without limiting the scope of this invention, some exemplary methods which can be used to produce non-stoichiometric materials, are:

Method 1: Start with submicron powders, preferably nanopowders. Transform the powders into a non-stoichiometric form by one or more of the following techniques—heating in inert atmosphere, heating in oxidizing atmosphere, heating in reducing atmosphere, solvent extraction, chemical reaction, electrochemical transformation, electromagnetic field treatment, ion beam treatment, electron beam treatment, photonic treatment, rapid quench, plasma treatment, nuclear radiation, supercritical phase treatment, biological treatment, or a combination of one or more techniques. Utilize the non-stoichiometric material so obtained. It may be desirable to sinter the non-stoichiometric powders into a solid. It may further be desirable to reconvert the non-stoichiometric material to a stoichiometric form.

Method 2: Produce non-stoichiometric powders, preferably nanopowders directly with techniques such as those taught in commonly assigned U.S. Pat. No. 5,788,738. Utilize the non-stoichiometric powders so obtained. For example, sinter and process them as appropriate. Finally, if desired, convert them to stoichiometric form.

Method 3: Mix nanoscale powders of a material and at least one of its components in a desired ratio and heat the combination in an inert or other appropriate atmosphere to a temperature that completes the solid state reaction. The material may comprise metallic, semimetallic, or non-metallic components, or any combination thereof. It may be possible to heat the materials in a reactive atmosphere to further control the ratio desired among the components in the final product. Utilize the non-stoichiometric substance so obtained.

Method 4: Add a dopant element with a valency different than one of the electropositive constituents in the substance in which non-stoichiometry is to be engineered. Heat the mix to a temperature greater than the solid state reaction temperature for a time that enables intermingling of the dopant element and the primary electropositive constituent. The objective in this procedure is to induce non-stoichiometry in a given substance because the distribution of secondary element introduces equivalent vacancies in the lattice of the substance.

Optimizing a Non-stoichiometric Material

This invention enormously multiplies the number of novel substance alternatives available for producing devices and products. A preferred embodiment of this invention is to optimize the composition of the non-stoichiometric substances for best performance. Such optimization may be accomplished by methods known in the art and by parallel search approaches such as the combinatorial search method taught by us in U.S. patent application Ser. No. 09/153,418 and by U.S. Pat. No. 5,776,359, both of which are incorporated by reference herein. One embodiment is to prepare samples of non-stoichiometric materials having different compositions and to evaluate the properties of the prepared samples. The material with the best performance is selected as having the preferred composition. Another embodiment is to prepare samples of non-stoichiometric materials having different compositions, process these samples into products, and evaluate each product's performance. Finally, the nanostructured non-stoichiometric material composition that gives the best performing product is selected as the preferred composition. In yet another embodiment, a product is prepared from a non-stoichiometric substance and the non-stoichiometry varied in-situ until the performance of the product is optimized with respect to the desired specifications. Other methods may be utilized to select the best composition. In all cases, it is important to consider all possible performance, environmental, and economic requirements of the product before a selection decision is made.

While the above approaches teach how to create and produce non-stoichiometric substances, useful products can be produced from nanostructured non-stoichiometric substances by techniques and methods already known in the art. For example, if a porous body is desired, mix the non-stoichiometric powders produced as above with an inert material and reprocess the mixture. As appropriate, add a processing step which would remove the inert material using techniques such as dissolution, sublimation, evaporation, leaching, chemical reaction, or biological action. This can lead to a porous body of nanostructured form.

If a given non-stoichiometric material is expensive to prepare, one can mix the non-stoichiometric powders produced as above with a stoichiometric material and reprocess the mixture. This may help reduce the processing costs required in conversion from and to stoichiometric form.

One embodiment of this invention is to use non-stoichiometric forms of materials as precursors for combinatorial discovery of materials and related technologies such as those disclosed in our commonly assigned U.S. patent application Ser. No. 09/153,418.

Another embodiment of this invention is to prepare devices from non-stoichiometric substances. Devices can be prepared using one of the manufacturing methods used currently in the art or a combination thereof. Examples of processes which can be used at some stage include but are not limited to pressing, extrusion, molding, screen printing, tape casting, spraying, doctor blading, sputtering, vapor deposition, epitaxy, electrochemical or electrophoretic deposition, thermophoretic deposition, centrifugal forming, magnetic deposition, and stamping. The non-stoichiometric material in the device can be porous or dense, thin or thick, flat or curved, covered with a barrier or exposed. As already mentioned, with the motivation of improved performance, stable performance, reduced costs, or a combination of these, non-stoichiometric materials may be converted partially or completely into a stoichiometric form or mixed with stoichiometric materials or both after being processed into a device.

Another embodiment of this invention is to prepare a device from stoichiometric materials and then convert the stoichiometric materials into a non-stoichiometric form. For example, a ferrite device can be prepared from stoichiometric magnetic materials which can then be transformed, partially or completely, into a non-stoichiometric form by heat treating the device in borane, ammonia, hydrogen, methane, or silane to form a non-stoichiometric boride, nitride, oxide, hydride, carbide, silicide, or a combination thereof In another example, a sensor or battery device can be prepared from stoichiometric electrochemical materials which can then be transformed, partially or completely, into a non-stoichiometric form by heat treating the device in borane, ammonia, hydrogen, methane, or silane to form a non-stoichiometric boride, nitride, oxide, hydride, carbide, silicide, or a combination thereof. In a third example, a display device can be prepared from stoichiometric photonic materials which can then be transformed, partially or completely, into a non-stoichiometric form by heat treating the device in borane, ammonia, hydrogen, methane, or silane to form a non-stoichiometric boride, nitride, oxide, hydride, carbide, silicide, or a combination thereof. In above examples in particular, and this embodiment in general, the heat treatment can be replaced by chemical methods, pressure, electrical methods, ion implantation, or any other method or combination of methods. In addition, a substrate may be incorporated into the device. The substrate on which electrodes are formed can be flat or curved, flexible or rigid, inorganic or organic, thin or thick, porous or dense. The preferred substrates are those that provide the mechanical properties needed for device life greater than the anticipated device usage life.

In some embodiments of the presently claimed invention, it may be desirable that the device be electroded. The electrode can be a wire or plate or coil, straight or curved, smooth or rough or wavy, thin or thick, solid or hollow, and flexible or non-flexible. For some device designs, for example, bead/pellet type device designs, it is preferred that the device is formed directly on the electrode wire or plate or coil instead of on a substrate. It is important in all cases that the electrode be conductive and stable at the usage temperatures. It is preferred that the electrode composition does not react with the non-stoichiometric substance or the environment during the manufacture or use of the device. The use of nanostructured forms of non-stoichiometric materials offers the benefit of sintering temperatures for devices which are lower than the sintering temperatures achievable with coarser grained form. This may enable the use of lower cost electrode materials (e.g., copper or nickel instead of gold or platinum). It is preferred that the non-stoichiometric form is non-agglomerated and of a form that favors sintering. It is also preferred that the melting point of the electrode is higher than the highest temperature to be used during the manufacture or use of the device. One of ordinary skill in the art will realize that other device architectures can also be used in the presently claimed invention. Furthermore, non-stoichiometric form of electrodes can be utilized to improve one or more performance parameters of the electrode in the device. Some examples of non-stoichiometric electrode substances are $NiO_{1-x}$, $NiO_{1-x}N$, $NiON_{1-x}$, $Cu_2O_{1-x}$, and $PdAgO_{1-x}$. The method described in this specification for preparing non-stoichiometric ceramics may be utilized for preparing non-stoichiometric electrode as well.

The device can be produced from various non-stoichiometric compositions, including ceramics, metals and alloys, polymers, and composites. The non-stoichiometric ceramics include but are not limited to binary, ternary, quaternary, or polyatomic forms of oxides, carbides, nitrides, borides, chalcogenides, halides, suicides, and phosphides. The invention also includes non-stoichiometric forms of ceramics, undoped and doped ceramics, and different phases of the same composition.

Metals and alloys such as those formed from a combination of two or more of s group, p group, d group and f group elements may be utilized. The invention includes non-stoichiometric forms of alloys, undoped and doped metals and alloys, and different phases of the same composition. Polymers of non-stoichiometric formulations include but are not limited to those with functional groups that enhance conductivity. Specific examples include but are not limited to non-stoichiometric composites with stoichiometric polymers, defect conducting polymers, and ion-beam treated polymers. One of ordinary skill in the art will realize that other polymers, such as metal-filled polymers or conducting ceramic-filled polymers, can also be used.

Device miniaturization is also a significant breakthrough that the presently claimed invention offers through the use of nanostructured non-stoichiometric materials. Existing precursors that are used to prepare devices are based on micron-sized powders. The mass of the device depends in part on the powder size because the device thickness cannot be less than a few multiples of the precursor powder size. In a multilayer device, each layer cannot be less than a few multiples of the precursor powder size. With nanostructured powders, the active element size and therefore its mass can be reduced significantly. For example, everything else remaining the same, the mass of a device can be reduced by a factor of 1000 if 10 nanometer powders are used instead of 10 micron powders. This method of reducing mass and size is relevant to devices in the electronics, electrical, magnetic, telecommunication, biomedical, photonic, sensors, electrochemical, instruments, structural, entertainment, education, display, marker, packaging, thermal, acoustic, and other industries. The presently claimed invention teaches that nanostructured non-stoichiometric powders are preferred to reduce the mass and size of a device.

EXAMPLES

Example 1

Indium Tin Oxide fillers in PMMA

A stoichiometric (90 wt % ln2O3 in $SnO_2$) indium tin oxide (ITO) nanopowder was produced using the methods of copending U.S. patent application Ser. No. 09/046,465. 50 g of indium shot was placed in 300 ml of glacial acetic acid and 10 ml of nitric acid. The combination, in a 1000 ml Erlenmeyer flask, was heated to reflux while stirring for 24 hours. At this point, 50 ml of $HNO_3$ was added, and the mixture was heated and stirred overnight. The solution so produced was clear, with all of the indium metal dissolved into the solution, and had a total final volume of 318 ml. An equal volume (318 mL) of 1-octanol was added to the solution along with 600 mL ethyl alcohol in a 1000 mL HDPE bottle, and the resulting mixture was vigorously shaken. 11.25 ml of tetrabutyltin was then stirred into the solution to produce a clear indium/tin emulsion. When the resulting emulsion was burned in air, it produced a brilliant violet flame. A yellow nanopowder residue was collected from the flamed emulsion. The nanopowder surface area was 13.5 $m^2/gm$, and x-ray diffractometer mean grain size was 60 nm.

Figure 2:
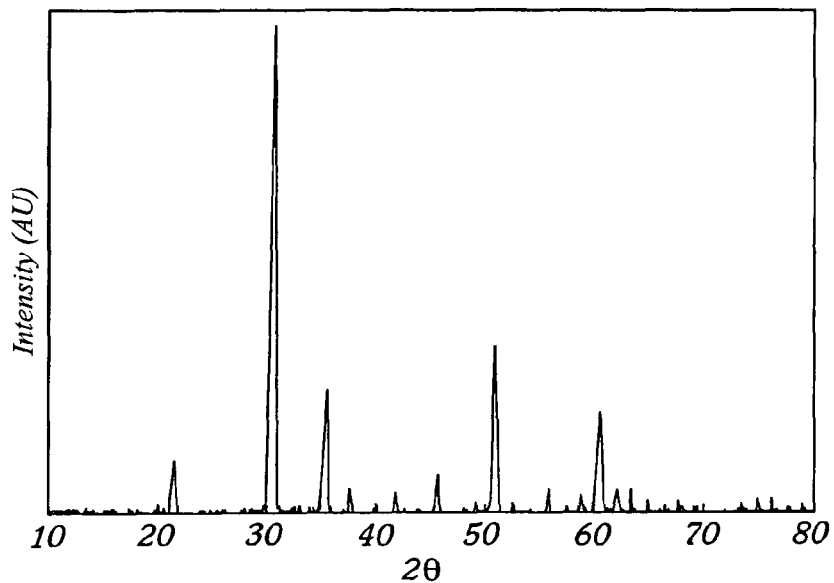
FIG. 2 portrays an X-ray diffraction (XRD) spectrum for the stoichiometric indium tin oxide powder of Example 1.
Figure 3:
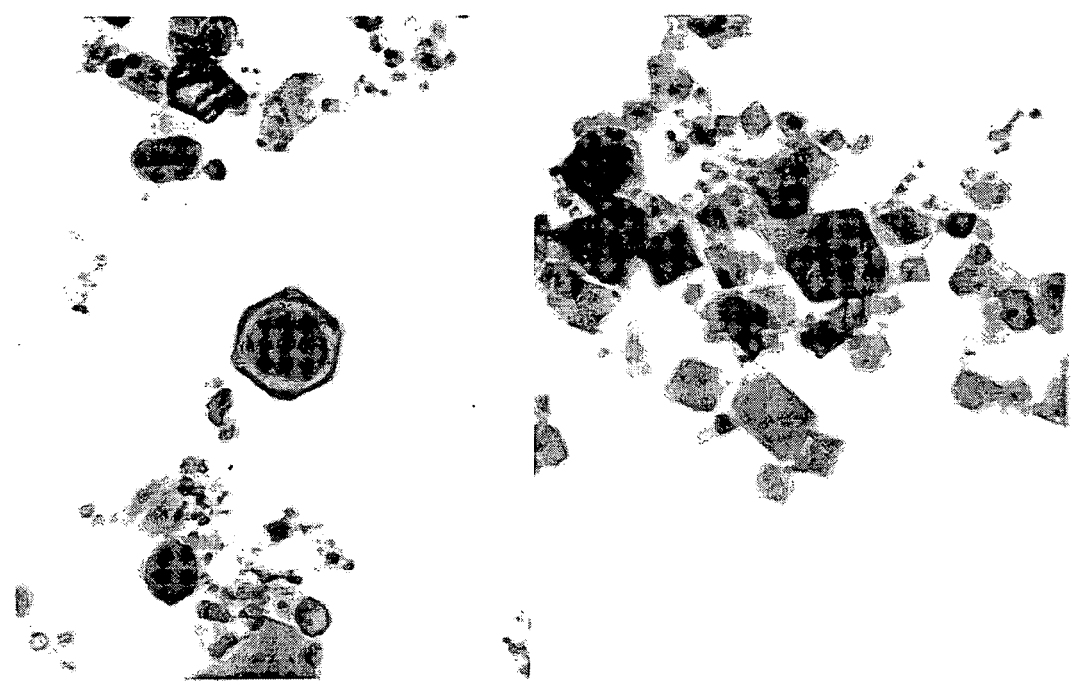
FIG. 3 is a scanning electron microscope (SEM) micrograph of the stoichiometric indium tin oxide powder of Example 1.

FIG. 2 shows the measured X-ray diffraction (XRD) spectrum for the powder, and FIG. 3 shows a scanning electron microscope (SEM image of the powder. These data show that the powder was of nanometer scale.

The nanostructured powder was then mixed with poly(methyl methacrylate) (PMMA) in a ratio of 20 vol % powder to 80 vol % PMMA. The powder and the polymer were mixed using a mortar and pestle, and then separated into three parts, each of which was pressed into a pellet. The pellets were pressed by using a Carver hydraulic press, pressing the mixture into a ¼ inch diameter die using a 1500 pound load for one minute.

After removal from the die, the physical dimensions of the pellets were measured, and the pellets were electroded with silver screen printing paste (Electro Sciences Laboratory 9912-F).

Pellet resistances were measured at 1 volt using a Megohmmeter/IR tester 1865 from QuadTech with a QuadTech component test fixture. The volume resistivity was calculated for each pellet using the standard relation, $$\rho = R\left(\frac{A}{t}\right) \quad (1)$$

where ρ represents volume resistivity in ohm-cm, R represents the measured resistance in ohms, A represents the area of the electroded surface of the pellet in cm², and t represents the thickness of the pellet in cm. The average volume resistivity of the stoichiometric ITO composite pellets was found to be $1.75 \times 10^4$ ohm-cm.

Another quantity of ITO nanopowder was produced as described above, and was reduced by passing 2 SCFM of forming gas (5% hydrogen in nitrogen) over the powder while ramping temperature from 25° C. to 250° C. at 5° C./min. The powder was held at 250° C. for 3 hours, and then cooled back to room temperature. The XRD spectrum of the resulting powder indicated that the stoichiometry of the reduced powder was $In_{18}SnO_{29-x}$, with x greater than 0 and less than 29.

The reduced ITO nanopowder was combined with PMMA in a 20:80 volume ratio and formed into pellets as described above. The pellets were electroded as described, and their resistivity was measured. The average resistivity for the reduced ITO composite pellets was found to be $1.09 \times 10^4$ ohm-cm.

For comparison, micron scale ITO was purchased from Alfa Aesar (catalog number 36348), and was formed into pellets with PMMA and electroded as described above. Again, the volume fraction of ITO was 20%. The average measured resistivity of the micron scale ITO composite pellets was found to be $8.26 \times 10^8$ ohm-cm, representing a difference of more than four orders of magnitude from the nanoscale composite pellets. It was thus established that composites incorporating nanoscale fillers can have unique properties not achievable by prior art techniques.

Example 2

Hafnium Carbide Fillers in PMMA

Composite pellets were produced as described in Example 1, by mixing filler and polymer with a mortar and pestle and pressing in a hydraulic press. Pellets were produced containing either nanoscale or micron scale powder at three loadings: 20 vol % powder, 50 vol % powder, and 80 vol % powder. The pellets were electroded as described above, and their resistivities were measured. (Because of the high resistances at the 20% loading, these pellets' resistivities were measured at 100 V. The other pellets were measured at IV, as described in Example 1).

Results of these resistivity measurements are summarized in Table 1. As can be seen, the resistivity of the pellets differed substantially between the nanoscale and micron scale powders. The composites incorporating nanoscale powder had a somewhat decreased resistivity compared to the micron scale powder at 20% loading, but had a dramatically increased resistivity compared to the micron scale powder at 50% and 80% loading.

TABLE 1

| Volume % filler | Resistivity of nanoscale powder composite (ohm-cm) | Resistivity of micron scale powder composite (ohm-cm) |
| --- | --- | --- |
| 20 | $5.54 \times 10^{12}$ | $7.33 \times 10^{13}$ |
| 50 | $7.54 \times 10^9$ | $2.13 \times 10^4$ |
| 80 | $3.44 \times 10^9$ | $1.14 \times 10^4$ |

Example 3

Copper Fillers in PMA and PVA

Nanoscale copper powders were produced as described in U.S. patent applications Ser. Nos. 08/706,819 and 08/707,341. The nanopower surface area was 28.1 m2/gm, and mean grain size was 22 nm. Micron scale copper powder was purchased from Aldrich (catalog number 32645-3) for comparison.

The nanoscale and micron scale copper powders were each mixed at a loading of 20 vol % copper to 80 vol % PMMA and formed into pellets as described above. In addition, pellets having a loading of 15 vol % copper in poly(vinyl alcohol) (PVA) were produced by the same method. The pellets were electroded and resistivities measured at 1 volt as described in Example 1. Results are shown in Table 2.

TABLE 2

| Additive | Polymer | Volume % filler | Volume Resistivity (ohm-cm) |
| --- | --- | --- | --- |
| nanoscale copper | PMMA | 20 | $5.68 \times 10^{10}$ |
| nanoscale copper | PVA | 15 | $4.59 \times 10^5$ |
| micron scale copper | PMMA | 20 | $4.19 \times 10^{12}$ |

It can be seen from Table 2 that the resistivity of the nanoscale copper powder/PMMA composite was substantially reduced compared to the micron scale copper powder/PMMA composite at the same loading, and that the resistivity of the nanoscale copper powder/PVA composite was lower still by five orders of magnitude.

Example 4

Preparation of Polymer-Coated Nanostructured Filler

The stoichiometric (90 wt % $In_2O_3$ in $SnO_2$) indium tin oxide (ITO) nanopowder of Example 1 was coated with a polymer as follows.

200 milligrams of ITO nanopowders with specific surface area of 53 m²/gm were added to 200 ml of demineralized water. The pH of the suspension was adjusted to 8.45 using ammonium hydroxide. In another container, 200 milligrams of poly(methyl methacrylate) (PMMA) was dissolved in 200 ml of ethanol. The PMMA solution was warmed to 100° C. while being stirred. The ITO suspension was added to the PMMA solution and the stirring and temperature of 100° C. was maintained till the solution reduced to a volume of 200 ml. The solution was then cooled to room temperature to a very homogenous solution with very light clear-milky color. The optical clarity confirmed that the powders are still nanostructured. The powder was dried in oven at 120° C. and its weight was measured to be 400 milligrams. The increase in weight, uniformity of morphology and the optical clarity confirmed that the nanopowders were coated with PMMA polymer.

The electrochemical properties of polymer coated nanopowders were different than the as-produced nanopowders. The as-produced nanopowder when suspended in demineralized water yielded a pH of 3.4, while the polymer coated nanopowders had a pH of 7.51.

Example 5

Preparation of Electrical Device Using Nanostructured Fillers

A complex oxide nanoscale filler having the following composition was prepared: $Bi_2O_3$ (48.8 wt %), NiO (24.4 wt %), CoO (12.2 wt %), $Cr_2O_3$ (2.4 wt %), MnO (12.2 wt %), and $Al_2O_3$ (<0.02 wt %). The complex oxide filler was prepared from the corresponding nitrates of the same cation. The nitrates of each constituent were added to 200 mL of deionized water while constantly stirring. Hydroxides were precipitated with the addition of 50 drops of 28-30% $NH_4OH$. The solution was filtered in a large buchner funnel and washed with deionized water and then with ethyl alcohol. The powder was dried in an oven at 80° C. for 30 minutes. The dried powder was ground using a mortar and pestle. A heat treatment schedule consisting of a 15 ° C./min ramp to 350° C. with a 30 minute dwell was used to calcine the ground powder.

The nanofiller was then incorporated at a loading of 4% into a zinc oxide ceramic matrix. The composite was prepared by mechanically mixing the doped oxide nanofiller powder with zinc oxide powder, incorporating the mixture into a slurry, and screen printing the slurry (further described below). For comparison, devices were made using both a nanoscale matrix powder produced by the methods of copending and commonly assigned U.S. patent application Ser. No. 08/706,819, and using a micron scale matrix powder purchased from Chemcorp. The fillers and the matrix powders were mixed mechanically using a mortar and pestle.

Using the filler-added micron scale powder, a paste was prepared by mixing 4.0 g of powder with 2.1 g of a commercial screen printing vehicle purchased from Electro Science Laboratories (ESL vehicle 400). The doped nanoscale powder paste was made using 3.5 g powder and 3.0 g ESL vehicle 400. Each paste was mixed using a glass stir rod. Silver-palladium was used as a conducting electrode material. A screen with a rectangular array pattern was used to print each paste on an alumina substrate. First a layer of silver-palladium powder (the lower electrode) was screen printed on the substrate and dried on a hot plate. Then the ceramic filled powder was deposited, also by screen printing. Four print-dry cycles were used to minimize the possibility of pinhole defects in the varistor. Finally, the upper electrode was deposited.

Figure 4:
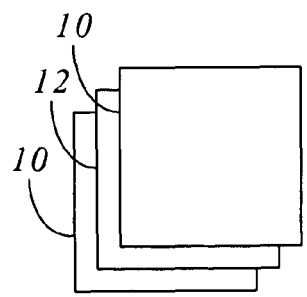
FIG. 4 is a diagram of the nanostructured varistor of Example 5.

The electrode/composite/electrode varistor was formed as three diagonally offset overlapping squares, as illustrated in FIG. 4. The effective nanostructured-filler based composite area in the device due to the offset of the electrodes was 0.036 $in^2$ (0.2315 $cm^2$). The green thick films were co-fired at 900° C. for 60 minutes. The screen printed specimen is shown in FIG. 4, where light squares 10 represent the silver-palladium electrodes, and dark square 12 represents the composite layer.

Silver leads were attached to the electrodes using silver epoxy. The epoxy was cured by heating at a 50° C./min ramp rate to 600° C. and then cooling to room temperature at a rate of 50° C./min. The TestPoint computer software, in conjunction with a Keithley® current source, was used to obtain a current-voltage curve for each of the varistors. Testpoint and Keithley are trademarks or registered trademark of Keithley Scientific Instruments, Inc.

The electrode/micron scale matrix composite/electrode based varistor device had a total thickness of 29-33 microns and a composite layer thickness of 19 microns. The electrode/nanoscale matrix composite/electrode based varistor device had a total thickness of 28-29 microns and a composite layer thickness of 16 microns. Examination of current-voltage response curves for both varistors showed that the nanostructured matrix varistor had an inflection voltage of about 2 volts, while the inflection voltage of the micron scale matrix varistor had an inflection voltage of about 36 volts. Fitting the current-voltage response curves to the standard varistor power-law equation $$I = nV^a \quad (2)$$

yielded values of voltage parameter a of 2.4 for the micron-scale matrix device, and 37.7 for the nanoscale matrix device. Thus, the nonlinearity of the device was shown to increase dramatically when the nanoscale matrix powder was employed.

Example 6

Thermal Battery Electrode using a Nanostructured Filler

Thermal batteries are primary batteries ideally suited for military ordinance, projectiles, mines, decoys, torpedoes, and space exploration systems, where they are used as highly reliable energy sources with high power density and extremely long shelf life. Thermal batteries have previously been manufactured using techniques that place inherent limits on the minimum thickness obtainable while ensuring adequate mechanical strength. This in turn has slowed miniaturization efforts and has limited achievable power densities, activation characteristics, safety, and other important performance characteristics. Nanocomposites help overcome this problem, as shown in the following example.

Three grams of raw $FeS_2$ powder was mixed and milled with a group of hard steel balls in a high energy ball mill for 30 hours. The grain size of produced powder was 25 nm. BET analysis showed the surface area of the nanopowder to be 6.61 $m^2/gm$. The TEM images confirmed that the ball milled $FeS_2$ powder consists of the fine particles with the round shape, similar thickness and homogenous size. The cathode comprised $FeS_2$ nanopowders (68%), eutectic LiCl—KCl (30%) and $SiO_2$ (2%) (from Aldrich Chemical with 99% purity). The eutectic salts enhanced the diffusion of Li ions and acted as a binder. Adding silicon oxide particles was expected to immobilize the LiCl—KCl salt during melting. For comparison, the cathode pellets were prepared from nanostructured and micron scale $FeS_2$ powders separately.

To improve electrochemical efficiencies and increase the melting point of anode, we chose micron scale Li 44%-Si 56% alloy with 99.5% purity (acquired from Cyprus Foote Mineral) as the anode material in this work. A eutectic salt, LiCl 45%-KCl 55% (from Aldrich Chemical with 99% purity), was selected as electrolyte. The salt was dried at 90° C. and fused at 500° C. To strengthen the pellets and prevent flowing out of electrolyte when it melted, 35% MgO (Aldrich Chemical, 99% purity) powder was added and mixed homogeneously with the eutectic salt powder.

The pellets of anode electrodes were prepared by a cold press process. A hard steel die with a 20 mm internal diameter was used to make the thin disk pellets. 0.314 grams of Li 44%-Si 56% alloy powder (with 76-422 mesh particle size) was pressed under 6000 psi static pressure to form a pellet.

The thickness and density of the pellets so obtained was determined to be 0.84 mm and 1.25 g/cm, respectively. Electrolyte pellets were produced using 0.55 grams of blended electrolyte powder under 4000 psi static pressure. The thickness and density of the pellets obtained were 0.84 mm and 2.08 g/cm² respectively. The cathode pellet was prepared using 0.91 grams of mixed micron scale $FeS_2$—LiCl—KCl—$SiO_2$ powder pressed under 4000 psi static pressure. The thickness and density of the pellets obtained were 0.86 mm and 3.37 g/cm², respectively.

A computerized SOLARTRON® 1287 electrochemical interface and a 1260 Gain/Phase Analyzer were employed to provide constant current and to monitor variation in potential between anode and cathode of cells during the discharging. "Solartron" is a registered trademark of the Solartron Electronic Group, Ltd. The cutoff potential of discharge was set at 0.8 volt. The thermal battery with the nanocomposite cathode provided 1 A constant current for 246 seconds, until the potential fell to 0.8 volt. It was observed that the power density of the nanostructured single cell thermal battery was 100% higher than that achievable with micron sized materials. Thus, nanoscale fillers can help enhance the electrochemical performance of such a device.

Example 7

A Magnetic Device Using Nanostructured Ferrite Fillers

Ferrite inductors were prepared using nanostructured and micron-scale powders follows. One-tenth of a mole (27.3 grams) of iron chloride hexahydrate ($FeCl_3$-$6H_2$ as O) was dissolved in 500 ml of distilled water along with 0.025 moles (3.24 grams) of nickel chloride ($NiCl_2$) and 0.025 moles (3.41 grams) of zinc chloride ($ZnCl_2$). In another large beaker, 25 grams of NaOH was dissolved in 500 ml of distilled water. While stirring the NaOH solution rapidly, the metal chloride solution was slowly added, forming a precipitate instantaneously. After 1 minute of stirring, the precipitate solution was vacuum filtered while frequently rinsing with distilled water. After the precipitate had dried enough to cake and crack, it was transferred to a glass dish and allowed to dry for 1 hour in an 80° C. drying oven. At this point, the precipitate was ground with a mortar and pestle and calcined in air at 400° C. for 1 hour to remove any remaining moisture and organics.

BET analysis of the produced powder yielded a surface area of 112 m²/g, confirming the presence of nanometer-sized individual particles with an estimated BET particle size of 11 nm. XRD analyses of all nanoscale powders showed the formation of a single (Ni, Zn)$Fe_2O_4$ ferrite phase with peak shapes characteristic of nanoscale powders. XRD peak broadening calculations reported an average crystallite size of 20 nm of the thermally quenched powders and 8 nm for the chemically derived powders. SEM-EDX analyses of sintered nanopowder pellets showed an average composition of 14.8% NiO, 15.8% ZnO, and 69.4% $Fe_2O_3$, which corresponded to the targeted stoichiometric composition of the $Ni_{0.5}Zn_{0.5}Fe_2O_4$.

Nanoscale ferrite filler powders were uniaxially pressed at 5000 pounds in a quarter-inch diameter die set into green pellets. The powders were mixed with 2 weight percent Duramax® binder for improved sinterability. The amount of powder used for pressing varied from 1.5 to 1.7 grams, typically resulting in cylinders having a post-sintered height of approximately 1.5 cm. To avoid cracking and other thermal stress effects, a multi-level heating profile was employed. The pellets were fired at a rate of 5° C./min to 300° C., 10° C./min to 600° C., and 20° C./min to the final sintering temperature, where it was held for four hours. Pellets were cooled from the sintering temperature at a rate of 10° C./min to ensure the sintering temperature ranged from 900° C. to 1300° C., but was typically greater than 1200° C. to ensure an acceptable density. Sintered pellets were then wound with 25 turns of 36 gauge enamel coated wire, the wire ends were stripped, and the completed solenoids where used for electrical characterization. An air coil was prepared for the purpose of calculating magnetic properties. This coil was created by winding 25 turns of the enamel coated wire around the die plunger used previously. This coil was taped with masking tape, slid off the plunger slowly to maintain shape and characteristics, and was characterized along with the ferrite solenoids.

Inductance characterization was performed with a Hewlett-Packard 429A RF Impedance/Materials Analyzer. Impedance, parallel inductance, q factor, and impedance resistance were measured over a logarithmic frequency sweep starting at 1 MHz and ending at 1.8 GHz. Values for permeability ($\mu$) and loss factor (LF) were calculated from inductance (L), air coil inductance ($L_o$), and impedance resistance (R) using the following equations:

$$\mu = \frac{L}{L_0} \tag{3}$$

$$LF = \frac{L_0 R}{\omega L^2} \tag{4}$$

Resistivity measurements were made with a Keithley® 2400 SourceMeter using a four-wire probe attachment and TestPoint™ data acquisition software. Voltage was ramped from 0.1 to 20 volts while simultaneously measuring current. The results were plotted as field (voltage divided by pellet thickness) versus current density (current divided by electrode cross sectional area). The slope of this graph gives material resistivity ($\rho$).

Table 3 summarizes electrical properties of inductors prepared from micron-sized powder or from nanopowder. In most cases there is an advantage to using nanoscale precursor powder instead of micron-sized powder. It is important to keep in mind that all measurements were taken from cylindrical devices, which have inherently inefficient magnetic properties. Solenoids of this shape were used in this study because of the ease of production and excellent reproducibility. All measured properties would be expected to improve with the use of higher magnetic efficiency shapes such as cores or toroids, or by improving the aspect ratio (length divided by diameter) of the cylindrical samples.

TABLE 3

| | Micron | Nano | | Micron | Nano |
|---|---|---|---|---|---|
| Loss Factor @ 1 MHz | | | Critical Frequency | | |
| Average | 0.0032 | 0.0025 | Average | 68.9 MHz | 78.3 MHz |
| Q Factor @ 1 MHz | | | Resistivity | | |
| Average | 37.2 | 52.2 | Average | 0.84 MΩ | 33.1 MΩ |

The inductors made from ferrite nanopowders exhibited significantly higher Q-factor, critical resonance frequency,

Example 8

Tungsten Oxide

Ammonium meta-tungstate (55 g) was placed in a 500 ml beaker with ethylene glycol (100 mL). This mixture was stirred to form a clear solution. While stirring, 500 mL of Igepal®. 520-CO and 500 mL of naphtha were added to the solution, yielding a clear emulsion tungstate/glycol solution (polar phase) in naptha (non-polar phase). The Igepal® 520-CO served as an emulsifying agent. Igepal is a registered trademark of Rhone-Poulenc Surfactants and Specialties, L.P.

Combustion of the emulsion produced an incandescent flame. A yellow powder, characteristic of tungsten oxide, was visible depositing within the combustion chamber. TEM and SEM observations indicated that the powder consisted of particles with both equiaxed (<100 nm) and acicular morphologies (e.g., 10×100 nm), and that the powder comprised solely sub-micron particles. These particle sizes are corroborated by X-ray diffraction data, suggesting crystallite sizes ranging from 14 to 33 nm for the primary peaks of the hexagonal $WO_3$ powder, a mean minimum domain size of about 25 nm and a standard deviation of about 7 nm. The specific surface area as measured by Brunauer, Emmett, and Teller analysis (described in more detail in Brunauer, et al., J. Am. Chem. Soc., 60:309, 1938, and hereinafter referred to as BET) was 31.5 $m^2/g$, giving a 30 nm equivalent spherical diameter. The experiment also produced $WO_3$ nanowhiskers and nanorods with aspect ratios ranging from 5 to 15.

Example 9

Tungsten-doped Tin Oxide

Ammonium meta-tungstate (7.95 g) was placed in a 500 ml beaker with ethylene glycol (10 mL). This mixture was stirred to form a clear solution. While stirring, 200 mL of Igepal® 520-CO and 200 mL of naphtha were added to the solution, yielding a clear emulsion tungstate/glycol solution (polar phase) in naptha (non-polar phase). The Igepal® 520-CO served as an emulsifying agent. Tetrabutyl tin (98.37 g) was added to the solution and naphtha was added to make a 700 mL volume.

Flaming of the emulsion produced an incandescent flame. A steel-blue powder was collected and characterized. The powder consists of faceted and equiaxed particles ranging from 10 to 75 nm showing solely sub-micron powder. Both nanowhiskers and equiaxed particles are present. The aspect ratios of the nanowhiskers were in the range of 3-20. Crystallite sizes as measured by X-ray diffraction range from 20 to 30 nm for the primary peaks of the $SnO_2$ powder, and there are no apparent secondary phases attributable to tungsten. The mean minimum domain size as calculated from the XRD data was about 27 nm and the standard deviation was estimated to be about 10 nm. The presence of tungsten was confirmed by X-Ray Electron Diffraction Spectroscopy (XEDS) both in the SEM and the TEM. The BET specific surface area was 35 $m^2/g$, giving an equivalent spherical diameter of about 20-30 nm.

Example 10

Copper Doped Nickel Zinc Ferrite

Commercially purchased metal-carboxylate emulsions (OMG Americas, Westlake, Ohio) were combined to form a clear emulsified solution that would yield the appropriate metal ratios to synthesize 300 g of the oxide. Flaming of the emulsion produced a brilliant incandescent flame. A chocolate-brown powder was collected and characterized. XRD data yielded crystallite sizes in the range of 20-40 nm, and indicated that the powder was a phase-pure spinel ferrite. The presence of all constituent elements was confirmed by XEDS in the SEM. The mean particle size of the powder was about 29 nm and the standard deviation was about 8 nm.

Example 11

Zinc

Commercially available zinc powder (−325 mesh) was used as the precursor to produce nanosize zinc powder. Feed zinc powder was fed into the thermal reactor suspended in an argon stream (argon was used as the plasma gas; the total argon flow rate was 2.5 $ft^3$/min). The reactor was inductively heated with 16 kW of RF plasma to over 5,000 K in the plasma zone and about 3,000 K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The nanosize powder produced by the invention were in the 5-25 nanometer range. The size distribution was narrow, with a mean size of approximately 15 nm and a standard deviation of about 7.5 nm.

Example 12

Iron-Titanium Intermetallic 2-5 micron powders of iron and 10-25 micron powders of titanium were mixed in 1:1 molar ratio and fed into the thermal reactor suspended in an argon stream (total gas flow rate, including plasma gas, was 2.75 $ft^3$/min). The reactor was inductively heated with 18 kW of RF plasma to over 5,000 K in the plasma zone and above 3,000 K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The nanopowders produced by the invention were in the 10-45 nanometer range. The size distribution was narrow, with a mean size of approximately 32 nm and a standard deviation of about 13.3 mn.

Example 13

Tungsten Oxide

Commercially available tungsten oxide powder (−325 mesh size) was used as the precursor to produce nanosize $WO_3$. The tungsten oxide powder was suspended in a mixture of argon and oxygen as the feed stream (flow rates were 2.25 $ft^3$/min for argon and 0.25 ft.sup.3/min for oxygen). The reactor was inductively heated with 18 kW of RF plasma to over 5,000 K in the plasma zone and about 3,000 K in the extended reactor zone adjacent the converging portion of the nozzle. The vaporized stream was quenched through the conand resistivity. They also exhibited more than 20% lower loss factor as is desired in commercial applications.

verging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The powder produced by the invention were in the 10-25 nanometer range. The size distribution was narrow, with a mean size of about 16.1 nm and a standard deviation of about 6.3 nm.

Example 14

Cerium Oxide

Commercially available cerium oxide powder (5-10 micron size) was used as the precursor to produce nanosize $CeO_2$. The cerium oxide powder was suspended in a mixture of argon and oxygen as the feed stream (at total rates of 2.25 $ft^3$/min for argon and 0.25 $ft^3$/min for oxygen). The reactor was inductively heated with 18 kW of RF plasma to over 5,000 K in the plasma zone and about 3,000 K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 650 Torr. The powder produced was separated from the gas by means of a cooled copper-coil-based impact filter followed by a screen filter. The powder produced by the invention was in the 5-25 nanometer range. The size distribution was narrow, with a mean size of about 18.6 nm and a standard deviation of about 5.8 nm.

Example 15

Silicon Carbide

Commercially available silicon carbide powder (−325 mesh size) was used as the precursor to produce nanosize SiC. The powder was suspended in argon as the feed stream (total argon flow rate of 2.5 $ft^3$/min). The reactor was inductively heated with 18 kW of RF plasma to over 5,000 K in the plasma zone and about 3,000 K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The SiC powder produced by the invention were in the 10-40 nanometer range. The size distribution was narrow, with a mean size of approximately 28 nm and a standard deviation of about 8.4 nm.

Example 16

Molybdenum Nitride

Commercially available molybdenum oxide ($MoO_3$) powder (−325 mesh size) was used as the precursor to produce nanosize $Mo_2N$. Argon was used as the plasma gas at a feed rate of 2.5 $ft^3$/min. A mixture of ammonia and hydrogen was used as the reactant gases ($NH_3$ at 0.1 $ft^3$/min; $H_2$ at 0.1 $ft^3$/min). The reactor was inductively heated with 18 kW of RF plasma to over 5,000 K in the plasma zone and about 3,000 K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The $Mo_2N$ powder produced by the invention was in the 5-30 nanometer range. The size distribution was narrow, with a mean size of about 14 nm and a standard deviation of about 4.6 nm.

Example 17

Nickel Boride 10-50 micron powder of nickel boride were fed into the thermal reactor with argon (fed at a total rate, including plasma gas, of 2.75 $ft^3$/min). Once again, the reactor was inductively heated with 18 kW of RF plasma to over 5,000 K in the plasma zone and about 3,000 K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The $Ni_3B$ powder produced by the invention was in the 10 to 30 nanometer range. The size distribution was narrow, with a mean size of about 12.8 nm and a standard deviation of about 4.2 nm.

Example 18

Processing of Materials

Densification of powders, or sintering, is essentially a process of removing the pores between the starting particles, combined with growth and strong bonding between adjacent particles. The driving force for densification is the free-energy change, or more specifically, the decrease in surface area and lowering of the free energy.

Among the processing variables that may affect the densification process, the particle size of the starting powder is one of the most important variables. In solid-state processes, assuming that the matter transport is controlled by lattice diffusion, the volume change of the material with respect to time during sintering can be related to processing variables as follows:

$$\frac{\_V}{V_o} = \left[ 3 \left( \frac{20 \gamma a^3 D^\circ}{\sqrt{2} kT} \right) r^{-1.2} t^{0.4} \right]$$

In this equation, $V_o$ and $\_V$ are the initial volume and volume change of the target during densification, respectively; T is the sintering temperature; t the sintering time; k the Boltzman constant, $D^\circ$ the self-diffusivity, $\gamma$ the surface energy of the particle, $a^3$ the atomic volume of the diffusing vacancy, and r the radius of the particle of the starting powder.

As we can see from the above equation, the sintering time needed to achieve a specific degree of densification is proportional to the cube of the particle size of the starting powder. Given the same sintering temperature and starting material, the densification rate can be increased drastically by using 100 nm sized powders instead of 10 nm sized powders. Alternatively, to obtain the same densification or to prevent the decomposition of a fragile material at high temperatures, sintering can be conducted at lower temperature with nano-structured powders. Thus, nano-sized materials can also significantly decrease the sintering temperatures currently used for micrometer-sized powders. From a commercial viewpoint, the energy savings from lower processing temperatures and the reduction of processing times can be substantial.

Another beneficial effect of using nano-sized powders is that, because of high surface area and surface diffusivity, nano-sized composites may be sintered without impurity inducing sintering aids, resulting in more reliable sintered products which exhibit enhanced service temperatures and high temperature strength. Other anticipated benefits described below include commercially attractive processing times and temperatures, lowered inventory costs, use of lower cost precursors, and the ability to sinter devices at temperatures that prevent undesirable secondary reactions or transformations during device fabrication. While this application prefers the use of nanopowders, the teachings herein can be applied to submicron and larger non-stoichiometric powders.

For example, put the non-stoichiometric material in a die and press the material to green densities of 40% or higher. Alternatively, use injection molding, CIP, HIP, electrophoretic, magnetophoretic, coatings, gel casting, dip coating, precipitation, thick film forming, molding, screen printing, extrusion, and any of techniques known in the art to form a body from the non-stoichiometric nanopowder prepared. Next, sinter the prepared body using a temperature, time, atmosphere, and electromagnetic field sufficient to reach desired density. If desired, the sintering step may be followed by machining or processing the densified form as appropriate. Finally, transform the densified and processed non-stoichiometric structure to stoichiometric form.

The motivation of this approach is explained above and further includes the following: The stoichiometric form of $M_{n/p}Z_{1-x}$ may be given by x=0 (i.e. $M_{n/p}Z$), the lower bound case of the inequality 0<x<1. When x=1, we get the upper inequality bound and this represents the pure element M. It is known to those skilled in the art that the sintering characteristics of M and $M_{n/p}Z$ are very different. Often, M is easier to consolidate and sinter than $M_{n/p}Z$. Thus, the use of $M_{n/p}Z_{1-x}$ is anticipated to offer performance intermediate to M and $M_{n/p}Z$. From a thermodynamic point of view, the unusual interfacial free energies of non-stoichiometric forms can allow the use of more commercially attractive sintering conditions (i.e. temperature, time, field, and atmosphere) to produce the product of interest. Also, by utilizing the non-stoichiometric form $M_{n/p}Z_{1-x}$, the unusual properties of the non-stoichiometric form can be beneficially applied to produce useful objects from powders or porous bodies.

For example, in the case of Ti and $TiO_2$, the sintering temperatures for metal and metal oxide are very different. Metals are easier to sinter and process metals than ceramics. It is expected that the sintering characteristics of a material form intermediate to the two extremes (x=0 and x=1) would also be different, in a linear or non-linear manner, than the two extremes. It is anticipated that non-stoichiometric forms of titania will be more reactive, that vacancies will assist pore volume reduction, and that these will reduce the time and temperature needed to density a structure.

Yet another example would be to use non-stoichiometric forms of doped or undoped superconductors, ferrites, carbides, borides, nitrides, alloys, and oxides, such as NiO, $BaTiO_3$, $ZrO_2$, and hafnia. The melting point of a metal is often less than that of the corresponding ceramic form. The use of non-stoichiometric compositions can assist in achieving dense forms at lower temperatures or reduce the time needed to densify a material at a given temperature.

In some applications, the unusual properties of non-stoichiometric material may suggest that the device be used in a non-stoichiometric form. However, such devices may change their performance over time or have other disadvantages. Such problems can be addressed through the use of protective coatings, secondary phases, and stabilizers.

Dense sputtering targets of various compositions can also be prepared using the above method. These targets can then be used to prepare thin films for electronic, information storage, optics, and various other products.

The motivation to use these teachings includes commercially attractive processing times and temperatures, lowered inventory costs, use of lower cost precursors, and the ability to sinter devices at temperatures that prevent undesirable secondary reactions or transformations during device fabrication.

Example 19

Catalysis

Nanopowders comprising 75% by weight indium tin oxide (ITO) (mean grain size: 12.9 nm, 60.9 $m^2$/gm) and 25% by weight alumina (mean grain size: 4.6 nm, 56 $m^2$/gm) were mixed and pressed into pellets weighing approximately 200 mg. The pellet was reduced in a 100 ml/min 5% H-95% Ar stream at 300° C. for 10 minutes. The yellow pellet became a bluish green color. The pellet was exposed to 12% methanol vapor in air (100 ml/min) at about 250° C. and the product gases analyzed using Varian 3600 Gas Chromatograph. The gas composition analysis indicated that the product gases contained 3400 ppm of hydrogen, suggesting catalytic activity from the non-stoichiometric blue green pellet. This is in contrast with the observation that the pellet showed no catalytic activity, every thing else remaining same, when the color was yellow. The blue green pellet was replaced with a platinum wire and the temperature raised to about 250° C. No catalytic activity was detectable for the platinum wire at this temperature. These observations suggest that the non-stoichiometric indium tin oxide has unique and surprising catalytic properties when contrasted with stoichiometric indium tin oxide.

Example 20

Photonics and Optics

Stoichiometric ITO (yellow, 30 nm mean grain size) was produced via the method of commonly assigned U.S. Pat. No. 5,788,738 by feeding ITO in air. Non-stoichiometric ITO (bluish black, 30 nm mean grain size) was produced using the method of commonly assigned U.S. Pat. No. 5,788,738 by feeding ITO in forming gas (5% hydrogen-95% argon). The nanopowders were dispersed in water and the UV-Vis absorption spectra were obtained.

It was observed that non-stoichiometry more than doubles the absorption of infrared wavelengths. This experiment suggests that the change in stoichiometry can be used to engineer and obtain unusual optical properties of a material.

Example 21

Electrical Devices

Titanium oxide nanopowders (white, 25 nm mean grain size) were heated in ammonia for 12 hours at 600° C. The nanopowders converted to a deep blue-black color corresponding to non-stoichiometric nanopowder form (28 nm mean grain size). The electrical conductivity of the non-stoichiometric nanopowders was found to be more than ten orders of magnitude higher (resistivity of $1.5\times10^{-2}$ ohm-cm) than the white titanium oxide nanopowders (greater than $10^8$ ohm-cm, which is effectively insulating). Electron microscopy on the blue-black powders revealed that the nanopowders were an oxynitride of titanium ($TiONx$). It is also of interest to note that commercially available micrometer-sized TiN powders exhibit a resistivity of about 1.5 ohm-cm, about two orders of magnitude higher than the non-stoichiometric nanopowder. Thus non-stoichiometry offers unusual non-linear properties. This example suggests the utility of non-stoichiometry and nanostructure to engineer dramatic changes in electrical properties.

Example 22

Magnetic Products

Nanoscale ferrite powders can be heated in ammonia or hydrogen or borane or methane to form non-stoichiometric ferrite. The powders can then be transformed into a form for incorporation into a device by techniques such as extrusion, tape casting, screen printing or any other methods or combination thereof.

As an illustration, three toroids composed of a nickel zinc ferrite material were sintered at 900° C. for 2 hours to obtain near-theoretical densities. Upon cooling, the toroids were wound with ten turns of 26 gauge enamel-coated copper wire. Magnetic properties, including impedance, resistance, and serial inductance, were tested from 10 Hz to 1 MHz with a Quadtech 7600 LCR meter and from 1 MHz to 1.8 GHz with a Hewlett-Packard Model 4291A Analyzer. In each case, measurement consisted of making a secure contact with the stripped ends of the windings on the sample toroids and performing a frequency sweep. Once tested, the three sample toroids were unwound and heated in a reducing atmosphere. Samples were ramped from room temperature to 800° C., held for one hour, then allowed to cool. During this cycle, a stream of 5% H-95% Ar flowed continuously over the samples. Upon recovery from the furnace, a noticeable change in sample color was observed. Previously a dark gray, the "reduced" ferrite toroids now had a lighter gray, mottled appearance. The reduced ferrite toroids were rewound with ten turns of the same wire and their magnetic properties were re-evaluated. The observed results indicated a surprising change in properties in the non-stoichiometric samples: for a reference frequency of 1 MHz, the resistance increased by 732%, the inductance changed by 12.8%, and the impedance reduced by 11.4%. That dramatic changes in resistance were observed and that the overall impedance of the devices remained largely unaffected by the non-stoichiometry implies that non-stoichiometry leads to a corresponding dramatic decrease in inductive reactance. In other words, non-stoichiometric ferrite cores exhibit higher magnetic loss. FIG. 2 shows an unusual change in resistance as a function of frequency, suggesting that the non-stoichiometry is changing the fundamental performance of the materials.

Yet another method of producing a magnetic device is as follows: 900 mg of manganese ferrite non-stoichiometric nanopowder and 800 mg of nickel zinc ferrite nanopowder are pressed at 90,000 psi in a quarter inch die. For all powders, 5 wt % Duramax® binder is added prior to pressing for improved sinterability. Pellets composed of nanopowders are sintered at 820° C. for 4 hours in a kiln with a 5° C./min ramping rate. Micrometer-sized reference pellets require sintering temperatures of 1200° C. or more for 4 hours, everything else remaining the same. After sintering, all pellet diameters are 0.6 cm, and pellet heights are about 1 cm. Each pellet is wound with 20 turns of 36 gauge enamel coated electrical wire. The final wound pellets are wrapped with Teflon tape to ensure that the windings stayed in place. These inductor samples can be characterized with an Impedance/Gain-phase Analyzer. The performance can be optimized by varying variables such as the aspect ratio, number of turns, composition, and grain size.

Example 23

Resistors and Resistor Arrays

Resistors are a mature technology and have served various industries for almost a century. They are produced in various forms and from various substances. Wire wound resistors are one of the oldest technologies used in the resistor market. The resistor is made by winding wire onto a ceramic bobbin or former. The wire materials are often alloys, and the diameter and length of the wire determine the resistivity. Metal foil resistors are prepared from metal foil that sometimes is less than one micrometer thick. The foil is stuck on a flat ceramic substrate and the resistance value engineered by precision etching a meandering pattern. These resistors are high value added and exhibit very low temperature coefficients of resistance. Film resistors are prepared by vapor deposition, anodization, or plating of metal or cermet or carbon film on a substrate, followed, if needed, by spiral cutting with a diamond wheel. Metal oxide resistors are prepared by depositing oxide vapor. Carbon film resistors are obtained by pyrolysis of hydrocarbon on ceramic substrates. Once again, spiraling is commonly used to achieve the desired resistance value. Some resistors are prepared from coating resistor inks consisting of a glass, metal particle dispersion in a viscous organic binder. The coating is stabilized by firing at temperatures around 600° C. The final resistance value is obtained by spiraling. These techniques are used for preparing discrete resistor chips, networks, or hybrid circuit systems. Desired resistance can be fine tuned by air abrasion. Conducting plastic resistors are similar to metal film oxide resistors. They differ in the fact that organic binder is here replaced with a plastic and that the dispersant is often carbon. Sintered structure resistors are prepared by sintering SiC or CrO with suitable dopants. These resistors are often used as thermistors, not as fixed linear resistors.

The presently claimed invention can be utilized in various embodiments for these devices. The composition of existing finished resistors can be transformed into non-stoichiometric forms a variety of techniques, such as heat treating (400° to 2000° C.) the device in a reducing, oxidizing, nitriding, boronizing, carburizing, or halogenating atmosphere, or a combination of these, over a period of time ranging from a few seconds to hours, shorter times being preferred. Alternatively, existing processes to manufacture these devices may be suitably modified at an intermediate stage with one or more different processing steps to yield a non-stoichiometric form. Another embodiment of this invention is to produce nanopowders of a non-stoichiometric substance and to then substitute the substance into existing processes and process it just as one would a stoichiometric substance.

For example, 65 $m^2$/gm $SiC_{0.8}$ nanopowders were produced and sonicated in polyvinyl alcohol. The resulting dispersion was then screen printed on alumina substrate. After printing, the elements were fired at approximately 300° C. for a half hour. The resistance of the resulting device was less than 1 megaohm. Addition of platinum and silver dopants reduced the resistance further. Both p-type and n-type behavior was observed depending on the dopant.

Arrays are produced by printing multiple elements. The motivation for printing arrays is to reduce the overall product size and to reduce the cost of placing multiple elements.

Example 24

Sensor Devices

Sensors are components which sense the component's environment or changes in the component's environment. The environment may include a state of mass, energy, momentum, charge, radiation, field, electrochemistry, biological form, or a combination of one or more of these. This example discusses how the teachings in the presently claimed invention can be utilized to design and practice better performing sensors, including chemical sensors. While the teachings here describe a single layer thick film, they apply to thing film and multilayer architectures as well.

In a chemical sensor, each crystallite of the sensing material has an electron-depleted surface layer (the so-called space charge layer) having a thickness "L" around it. This length is determined by the Debye length and the chemisorbed species, and can be approximated by the following expression:

$$L = L_D \sqrt{\frac{2eV_s}{kT}}$$

where,
$L_D$: intrinsic value of space charge thickness;
$eV_s$: height of Schottky barrier at grain boundaries (depends on the sort and amount of adsorbates);
k: Boltzmann's constant; and
T: temperature.

If the crystallite size "D" is greater than twice the space charge layer thickness "L," which is always true for sensors based on existing micrometer-size grained stoichiometric materials, the electrical resistance of the sensor device is determined by the electron transport across each grain boundary, not by the bulk resistance. The resistance in this regime can be expressed as:

$$R = R_o \exp\left(\frac{eV_s}{kT}\right)$$

where $R_o$: bulk resistance.

The generally accepted definition of device sensitivity of a device is given by (or is a simple variation of):

$$S = \frac{R_g}{R_a} = \frac{R_o \exp\left(\frac{eV_{sg}}{kt}\right)}{R_o \exp\left(\frac{eV_{sa}}{kt}\right)} = \exp\frac{e\_V_s}{kT}$$

where,
$R_a$: resistance of device in air; and
$R_g$: resistance of device in air containing an analyte.

Because "$e\_V_S$" is independent of "D" until "D" is greater than twice the space charge layer thickness "L," it is no surprise that the observed sensitivity of the sensor device is independent of crystallite size in this regime. The above arguments lead to the natural question: what happens when D<2L? In this nanoscale regime, the device resistance is no longer just grain boundary controlled; instead, the bulk resistance of each grain becomes important. Since, "$e\_V_S$" is dependent on the adsorbate type and amount, this change in phenomenological regime provides an unprecedented way to engineer extremely sensitive sensors. In effect, one can engineer the crystallite size and the non-stoichiometry such that $R_g$ becomes bulk grain controlled (i.e., very high), while $R_a$ remains grain boundary controlled (i.e., low). This changes "$e\_V_S$" significantly, and since the sensitivity "S" depends exponentially on "$e\_V_S$," this can dramatically enhance the sensitivity of the sensor device. Enhanced sensitivity has been long sought in the sensor industry.

The benefits of nanostructured non-stoichiometric fillers may be exploited in monolithic or composite form. A composite, loosely defined, is a combination of two or more dissimilar materials, or phases, combined in such a way that each material maintains its individual character. The properties of the composite depend greatly on the arrangement of the individual phases present. In completely homogeneous composites, the properties tend to be a combination of the properties of the distinct phases present, a combination that is often unobtainable with metals, ceramics, or polymers alone. This makes composites unique and very appealing for applications which require a demanding and conflicting matrix of design needs. Sensors are one such application where conventional materials in monolithic form often excel in meeting some design goals, but fail to meet others. Composites of nanoscale non-stoichiometric substances can potentially provide the breakthrough where all the needs are simultaneously met. This embodiment is particularly useful when the selectivity of the sensor needs improvement.

Sensors (and sensor arrays) can prepared by numerous methods and the benefits of nanoscale non-stoichiometric substances can be practiced with any of these methods. In one embodiment, sensing films were prepared by brushing on a slurry containing nanoscale non-stoichiometric powders (and polymer, if appropriate) onto a screen-printed electrode on a substrate. The sensor electrodes were prepared using a Presco Model 465 Semi-Automatic Screen Printer. This equipment facilitated automatic printing, with the exception of loading and unloading the substrate. The screen used was from Utz Engineering, Inc. The screen was made from stainless steel mesh and had a frame size of 8×10 inches, a mesh count of 400, a wire diameter of 0.0007 inches, a bias of 45 degrees, and a polymeric emulsion of 0.0002 inches. The gold electrodes were screen printed on a 96% alumina substrate and then fired in air at 850° C. for a peak time of 12 minutes. Dopant polymers were dissolved in an appropriate solvent. Once the polymer was dissolved, non-stoichiometric nanopowders were added to the solution and sonicated for 20 minutes. The slurry was then deposited onto an electrode using a small paint brush. Once deposited, the elements were allowed to dry in air at 100° C. for 30 minutes to remove the solvent.

In an alternate embodiment, a screen printable paste was first prepared. The paste was again prepared from nanopowder and polymer. The nanopowder, polymer, and catalyst (when included) were weighed out and mixed together in a mortar and pestle. Next, screen printing vehicle was weighed out and transferred to the mortar and pestle where the two phases were mixed together. Finally, this paste was placed on a three roll mill and milled for five minutes. The three roll mill allowed for high shear mixing to thoroughly mix the paste and to break up agglomerates in the starting nanopowder. After the paste was prepared it is screen printed on to the prepared electrodes, allowed to level, and then dried at 100° C. This embodiment illustrates a method for preparing single elements and arrays of sensors.

Next, the sensing elements were screened, tested, and optimized for sensitivity, selectivity, and response time, as described below.

The sensitivity is calculated from the change in resistance of the sensor when exposed to a background and when exposed a vapor analyte species in background and determines the threshold exposure levels. A simple variation of the above equation describing sensitivity is:

$$\text{Sensitivity} = \frac{R_a - R_s}{R_s}$$

where:
$R_a$=sensor resistance in background; and
$R_s$=sensor resistance when exposed to analyte vapor.

The selectivity is a comparison of either the sensitivity of an individual sensor to two different analytes or of two sensors to the same analyte.

$$\text{Selectivity} = \frac{\text{Sensitivity}_a}{\text{Sensitivity}_b}$$

The response time is the time it takes for the sensor to detect a change in the surrounding environment, defined as the time required for the sensor to reach 90% of its peak resistance ($R_s$).

With non-stoichiometric nanoscale powders, low temperature sensing elements with sensitivity S greater than 1.5, selectivity greater than 1.1, and response times less than 10 minutes can be obtained for wide range of gaseous and liquid analytes. With optimization, selectivity greater than 2, sensitivity greater than 1.5, and response time less than 1 minute can be obtained at ambient conditions.

Some specific examples of analytes that can be sensed using the teachings herein, include, but are not limited to: carbon oxides (CO, $CO_2$), nitrogen oxides ($NO_x$), ammonia, hydrogen sulfide, borane, hydrogen, hydrazine, acidic vapors, alkaline vapors, ozone, oxygen, silane, silicon compounds, halogenated compounds, hydrocarbons, organic compounds, metallorganic compounds, metal vapors, and volatile inorganics.

Example 25

Biomedical Products

Mechanical alloying can be used to prepare nanocrystalline non-stoichiometric alloys. The feed powder Ti-4.9Ta-11Nb-15.2Zr is loaded in non-stoichiometric proportions into a cylindrical hardened steel vial with hardened steel mill balls. The ball-to-powder ratio is preferably high (5:1). The loading process is preferably done within an argon atmosphere glove box. The environment inside is maintained at an oxygen concentration of <100 PPM and moisture content of <3.0 PPM. The mill itself is set up outside of the glove box and the vial and mill housing cooled using forced air convection. After milling, the vial is transferred back to the glove box where the non-stoichiometric powder is collected and submitted for analysis or further processing. To prepare an orthopedic implant, the synthesized powders are uniaxially pressed. Poly(ethylene glycol) (PEG) may be used as a binder for compaction of the powders. PEG is added to the powders by preparing a 1 weight percent solution in ethanol and wet mixing the solution with the alloyed powders. The homogeneous mixture is air dried at room temperature. A press can be used to compact the powders in a die. A uniaxial 11,250 lb. force is applied (resulting in 225,000 psi of pressure) which is appropriate for implant specimens.

One advantage of non-stoichiometric nanoscale powders is the potential use of non-toxic elements in orthopedic and other biomedical implants. In general, biomedical implants are engineered to control properties such as strength, toughness, modulus, corrosion resistance, biocompatibility, porosity, surface roughness, and wear resistance. The materials described in the previous paragraph can be optimized to match the modulus of bone, a desirable characteristic of materials for some joint replacement applications. In other embodiments, nanopowders can be utilized for drug delivery and as markers for diagnosis. Nanopowders can also be utilized for enhancing the solubility of drugs in organic and inorganic solvents. In yet other embodiments, the teachings can be applied to various products where inorganic and organic powders are currently being utilized, as known to those skilled in the art.

Example 26

Electronic Components

Electronic components, for example, disc and multilayer capacitors, inductors, resistors, filters, antennas, piezo devices, LED, sensors, connectors, varistors, thermistors, transformers, current converters, shields, or arrays of such components in conventional mount or surface mount form, can be prepared using the teachings herein. As an example, to prepare varistors from nanoscale non-stoichiometric materials, a paste of the powders was prepared by mixing the powder and screen printing vehicle with a glass stir rod. Exemplary compositions include $ZnO_{1-x}$, $Bi_{2/3}O$, and other oxides. Silver-palladium was used as the conducting electrode material. A screen with a rectangular array pattern was used to print the paste on an alumina substrate. The process consists of screen printing the electrode and rapidly drying the film on a heated plate. The process was attended and precautions taken to prevent electrically shorting the device. The final electrode was applied in the same manner as the first. The effective non-stoichiometric nanostructured-filler based composite area in the device due to the offset of the electrodes was small (0.2315 cm$^2$). However, this offset may be increased or further decreased to suit the needs of the application. The thick green films were co-fired at 900° C. for 60 minutes.

Such a device offers a means to control surge voltages. An accurate determination of device non-linearity, α, can be obtained using the empirical varistor power law equation:

$$I = nV^\alpha$$

where: I=current.
n=the varistor power coefficient.
V=voltage.

The value of α obtained for the nanostructured non-stoichiometric device is anticipated to be 10 fold higher than that achievable with micrometer-sized stoichiometric fillers. It is also expected that the resistance of the boundaries would be lower, enabling clamping capability of lower voltages and higher frequencies. Other components that can specifically benefit from the high surface area of nanostructured non-stoichiometric materials include but are not limited to positive temperature coefficient resistors and barrier layer capacitors.

Example 27

Electrochemical Products

Electrochemical products, for example, batteries, electrolytic cells, corrosion inhibitors, electrodes in metallurgical applications and other industries, pH sensors, and electrochemical sensors, can benefit from the use of non-stoichiometric nanopowders. The most distinctive feature of these non-stoichiometric nanopowder materials is their unique thermodynamic state and the large number of atoms situated in the interfaces. A 10 nm nanocrystalline metal particle contains typically $10^{25}$ atoms which are situated on or near the interface per cubic meter of material; thus, 30% of total atoms in the material are situated in the interfaces or on the surface and exhibit non-bulk properties. Such a unique ultra-fine structure of nanopowders, when applied to electrochemical products, can lead to a drastic improvement of their performance. The ultra-fine (nanometer scale) microstructure of nanostructured hydrogen storage materials, to illustrate, will not only enhance the thermodynamics and kinetics of hydriding and dehydriding processes, but also improve their structure stability, and thus reliability and life time.

Particularly, nanostructured materials offer the following motivation for their utilization:

(i) Drastic Increase of Species Solubility or Capacity

The ultra-fine grain size of nanostructured materials gives an excess Gibbs free energy to the system compared to the conventional large grained (micrometer size) hydrides. This will significantly enhance the solubility of solute atoms, including hydrogen, because:

$$\frac{C_d}{C_\infty} = \frac{kV}{RT}\frac{\sigma}{d}$$

where:
$C_d$ and $C_\infty$=solubilities of a solute in the material with average grain size d and infinite grain size, respectively;
R=gas constant;
T=temperature;
V=the molar volume of the solute;
k=Boltzmann's constant;
σ=the surface energy of the grain.

Thus, theoretically, a 10 nm grained hydride is expected to have a hydrogen solubility 1000 times higher than a 10 μm grained hydride with the same chemical composition. The use of non-stoichiometric nanoscale powders offers to further enhance the thermodynamic and/or kinetic potential of the system. Other advantages of non-stoichiometric formulations, for example, faster and more economical processing conditions, still apply.

(ii) Significant Enhancement of Hydrogen Diffusivity

The large volume fraction of interface in nanostructured materials will result in grain boundary diffusion dominating the overall diffusion in the materials. The overall or effective diffusivity of solute atoms in the material is given by:

$$D^{\mathit{eff}} = fD_{gb} + (1-f)D_{lt}$$

where: $D^{\mathit{eff}}$=the effective or overall diffusion coefficient;
$D_{gb}$=the diffusion coefficient in grain boundaries;
$D_{lt}$=the diffusion coefficient within grains.
f=the fraction of solute atoms on the grain boundaries.

Since $D_{gb}$ normally is $10^4$ times higher than $D_{lt}$, or $D_{gb} \gg D_{lt}$, and more than 30% of atoms are situated in the grain boundaries, the above equation can be rewritten as $$D^{\mathit{eff}} \approx fD_{gb} = 0.3 D_{gb} \ll D_{lt}$$

The solute diffusion coefficient in nanostructured materials, therefore, is expected to be 1000 to 10,000 times higher than in conventional micro-grained materials.

(iii) Reduction of Temperature and Pressure for Hydride Formation and Dissociation The excess free Gibbs energy due to the ultra-fine structure of nanomaterials will also lead to significant change in phase transformation temperatures such as the hydride formation temperature. The phase transformation temperature change _T due to the ultrafine structure is related to the grain size d by:

$$\_T = \frac{(\sigma_1 - \sigma_2)T_c}{L}\frac{k}{d}$$

where:
$\sigma_1, \sigma_2$=specific surface energies of phase 1 and phase 2, respectively;
L=the heat of transformation from phase 1 to phase 2;
$T_c$=the phase transformation for the bulk material;
k=Boltzmann's constant.

Thus, the phase transformation temperature is expected to change as the grain size decreases. Because the hydrogen dissociation pressure decreases as the dissociation temperature decreases, the ultra-fine microstructure of nanostructured materials in general, and non-stoichiometric nanomaterials in particular, is preferable design guideline to a lower hydrogen dissociation pressure. This is very desirable in hydrogen storage technologies. This basic guideline for practice applies even to other electrochemical couples and systems such as batteries and electrodes. The benefits of lower phase transformation temperature have utility beyond electrochemical products and apply to thermal (e.g. heat transfer fluids) and other applications as well.

(iv) Higher Resistance to Pulverization During Hydriding/dehydriding Processes

High strength is essential to pulverization resistance due to large lattice expansion and contraction during hydriding/dehydriding processes. The ultrafine grain size of nanostructured hydrides offers a drastic improvement in their structure stability. This can be inferred from the yield strength of a material which is related to its grain size d by the Hall-Petch relationship:

$$\sigma_y = \sigma_o + \frac{k_y}{\sqrt{d}}$$

Fracture toughness, $K_{IC}$, is related to grain size by:

$$K_{IC} = \sigma_y \sqrt{\pi a_c}$$

where:
$\sigma_y$=the yield strength;
$\sigma_o$=the frictional stress needed to move the dislocation;
$k_y$=a constant;
$a_c$=the critical crack length.

This indicates that as the grain size decreases from 10 µm to 10 nm, both the strength and fracture toughness are expected to increase by a factor of 30, which in turn leads to a higher resistance to pulverization. Thus, electrochemical products in particular, and other products in general, can benefit from superior performance of nanostructured materials.

Some specific examples for the use of non-stoichiometric nanomaterials in electrochemical products would be rare-earth doped or undoped $Mg_{1.8}Ni$, $Ni$—$ZrNi_{1.6}$, $La_{0.9}Ni_5$, and other existing compositions with non-stoichiometry as explained previously.

Example 28

Energy and Ion Conducting Devices

Stoichiometric nanoscale 9 mole % yttria-stabilized cubic zircornia powders ($Y_{18}Zr_{91}O_{209}$) are first reduced at moderate temperatures (500° to 1200° C.) in a forming, or reactive, gas to yield non-stoichiometric $Y_{18}Zr_{91}O_{185}$ nanopowders. These powders are pressed into 3 mm diameter discs and then sintered to high densities. The disks should be preferably sintered at low temperatures (preferably 800 to 1200° C.) for short times (preferably 6 to 24 hours) to minimize grain growth. These nanopowders, as discussed before, can be readily sintered to full theoretical densities (99% or more). Careful control and optimization of the sintering profile and time can reduce the sintering temperature and time further. The two ends of the cylindrical discs so produced are then coated with a cermet paste consisting of a mix of silver and nanoscale stoichiometric yttria stabilized zirconia powder (a 50-50 wt % mix). Non-stoichiometric nanoscale powders can be utilized in the electrode as well. Platinum leads are then attached to the cermet layer. This device can serve as an oxygen-conducting electrolyte with significantly higher oxygen ion conductivity at lower temperatures than conventional electrolytes. Exemplary devices include but are not limited to oxygen sensors, oxygen pumps, or fuel cells. In this example, the degree of non-stoichiometry is arbitrarily chosen, and further optimization can be beneficial to the economics and performance.

The benefits of this invention can be utilized even when the yttria in the zirconia formulation is replaced with other stabilizers such as scandium oxide, calcium oxide, and other oxides. Similarly, other Group IV oxides (e.g. ceria) and perovskites can be used instead of zirconia. Other ion conductors, for example, beta alumina and NASICONs for sodium ion, lithium nitride and LISICONs for lithium ions, silver iodide for silver ions, $Rb_4Cu_{16}I_7Cl_{13}$ for copper ions, polymers such as nafion and perovskites for hydrogen protons, can all benefit from the use of non-stoichiometry in the ion conducting electrolytes and/or electrodes.

Example 29

Dopants in Formulations and Inks

Often, it is necessary to add secondary phase particles to a primary powder element to achieve a desired property, such as temperature coefficient of the dielectric constant. For example, commercial capacitor formulations of the Electronic Industry of America (EIA) X7R designation contain additions of dopants (e.g. tantalum oxide, niobium oxide, nickel oxide, bismuth oxide, silicates, titanates, and manganese oxide) which are added to the base barium titanate powder to tailor the temperature-capacitance or other characteristics of the material. The secondary phase particle additions are also often used to facilitate low temperature sintering. These materials include, but are not limited to, bismuth oxide, copper oxide, titanium oxide, silicon oxide, and vanadium oxide.

In these powder mixtures, it is usually desirable to achieve a uniform mixture of the primary phase particles and the secondary phase particles. This can be difficult if the volume fraction of the secondary particles is small and if the size of the secondary particles is large in relation to that of the primary particles. The problem is that the number fraction of the secondary particle phase is small in relation to that of the primary particle phase; thus, the relative distances between the secondary phase particles can be rather large. This can translate to a non-uniform distribution of the secondary phase particle species throughout the powder element and also in the microstructure of the final product.

Nanocrystalline powders in general and non-stoichiometric powders in particular produced by any technique can reduce the size of the secondary particles relative to primary particles and in turn, increase the number fraction of the secondary particles in the powder element. This will translate to a uniform mixedness in the powder element and in the product's microstructure.

To illustrate, 80 nm (preferably 40 nm, more preferably 10 nm) $Ta_{2/3}O_{0.9}$, $Nb_{b\ 2/5}O_{0.74}$, $NiO_{0.98}$, $Mn_{1/2}O_{0.9}$, $Bi_{2/3}O_{0.45}$, $Cu_{1.9}O$, $TiO_{1.1}$, $SiO_{1.55}$, and $V_{2/5}O_{0.975}$ are examples of non-stoichiometric nanopowders that can be used as dopants in device formulations and inks.

Example 30

Chemical Sensors

This example is from U.S. patent application Ser. No. 09/153,418 which was incorporated in this specification and is herewith presented for convenience.

An array was formed from the following components: (1) Nanostructured $SnO_2$ powder; (2) Nanostructured TiON powder; (3) Polyvinyl chloride (PVC); and (4) Polyaniline (PAN).

The $SnO_2$ nanopowders were prepared as follows: First, 25 g of $SnCl_4 \cong 5H_2O$ was dissolved in 120 ml of deionized water and then 120 ml of denatured alcohol was added to the solution. Next, a solution of 14% $NH_4OH$ was prepared from 28-30% $NH_4OH$ and deionized water. Both solutions were then placed in a freezer at approximately −5° C. for 30 minutes. The solutions were then removed from the freezer and the $SnCl_4$ solution was precipitated, forming $Sn(OH)_4$, dropwise under constant stirring with the $NH_4OH$ solution. As the solution thickened the stir rate was increased and a glass rod was used to break up the gelatinous mixture. The precipitation was continued until the pH of the solution was approximately 9. The precipitate was then vacuum filtered in a 3 L Buchner funnel. It was washed several times with deionized water, then several times with denatured alcohol to minimize agglomeration. The precipitate was then collected from the filter and dried at 100° C. for two hours and ground with a mortar and pestle to a fine powder. The powder was heated at 20 EC/minute to 450° C. and calcined for 30 minutes, forming nanopowders of $SnO_2$. The TiON was prepared by reducing nanoscale titania ($TiO_2$) (Degussa $TiO_2$ as received) in an ammonia ($NH_3$) stream in a rotating furnace at 750° C. for 24 hours. Polymers used were obtained from Sigma-Aldrich and used as received.

To prepare the sensors, electrodes were prepared on an alumina substrate by screen printing, using a semi-automatic screen printer. This equipment facilitates automatic printing, requiring manual intervention only for loading and unloading the substrate. The screen used was from Utz Engineering, Inc. The screen was made from stainless steel mesh and has a frame size of 8×10 inches, mesh count of 400, wire diameter of 0.0007 inches, bias of 45 degrees, and a polymeric emulsion of 0.0002 inches.

Gold screen printing paste (Electro Sciences Laboratory, #8835-1B) was used for the electrodes. They were printed on 10 mil thick, 96% alumina substrates laser scribed into ¼"× ¼" sections for easy separation (Laserage Technology Corporation). Once printed the electrodes were allowed to level, dried at 100° C. for 10 minutes and finally fired at a peak temperature of 850° C. for 12 minutes. Then, 0.5 grams of $SnO_2$ nanopowder was suspended in 2 ml of isopropanol by sonicating for 20 minutes. The active sensing layer was then deposited by using a pipette to place two drops of the slurry onto the electrode. This was then allowed to dry at 100° C. and finally fired at 400° C.

To prepare the arrays, screen printable pastes were first prepared as follows:

1. 98/2 (by weight) $SnO_2$/Polyaniline+catalyst 2.11 grams SnO2 nanopowder, 0.05 grams PAN, 0.04 grams Palladium acetate (Aldrich, 98%, 20,586-9) and 0.05 Dihydrogen hexachloroplatinate (Alfa-Aesar, 11051) were weighed out and mixed together in a mortar and pestle. Next, 1.1 grams of screen printing vehicle (Electro-Sciences Laboratories, #400) was weighed out and transferred to the mortar and pestle where the two phases were mixed together. Finally, this paste was placed on a three roll mill and milled for five minutes. The three roll mill allowed for high shear mixing to thoroughly mix the paste and to break up agglomerates in the starting nanopowder.

2. 98/2 (by weight) $SnO_2$/Poly(vinyl chloride)+catalyst 0.03 grams of Palladium powder (Aldrich, submicron, 32,666-6) was added to 2.37 grams of a paste prepared as above, substituting poly(vinyl chloride) for PAN. The paste was placed on a three roll mill and milled for five minutes.

3. 98/2 (by weight) TiON/Polyaniline+catalyst 3.00 grams TiON nanopowder, 0.06 grams PAN, 0.11 grams Palladium acetate (Aldrich, 98%, 20,586-9) were weighed out and mixed together in a mortar and pestle. Next, 1.5 grams of screen printing vehicle (Electro-Sciences Laboratories, #400) was weighed out and transferred to the mortar and pestle where the two phases were mixed together. Finally, this paste was placed on a three roll mill and milled for five minutes. The three roll mill allowed for high shear mixing to thoroughly mix the paste and to break up agglomerates in the starting nanopowder. After the paste was prepared it was screen printed onto the prepared electrodes, using a Presco Model 465 Semi-Automatic Screen Printer, allowed to level and then dried at 100° C. The sensors were then thermally treated, at 250° C., to activate the Palladium acetate to PdO.

The pastes prepared were screen printed, one at a time, onto three adjacent electrodes using a Semi-Automatic Screen Printer. The fourth element was baseline and blank. The active printed elements were allowed to level, dried at 100° C. for 10 minutes and finally thermally treated at 250° C.

For testing of the arrays the sensors' resistance were allowed to stabilize in a background of 200 ml/min of air at room temperature. The test was begun and background data was taken for 1 minute. Then, the 200 ml/min air flow was switched to flow through a bubbler containing either Sigma Pseudo Explosive Scent, nitrotoluene or cyclohexane. Air passing through the bubbler picked up analyte vapor and then passed into the testing unit. Data was collected for 3 minutes. Finally, the flow was returned to 200 ml/min of plain air and data were collected for 2 minutes.

The resistance of the array was measured simultaneously in parallel using a resistance meter and a printed circuit board. The testing unit allowed the determination of composite resistance and individual resistances as different gases were passed over the array.

It was found that the $SnO_2$/PVC+Pd catalyst could sense nitrotoluene vapors; the other formulations had no response to nitrotoluene vapors. $SnO_2$/PVC+Pd catalyst and $SnO_{21}$/PAN+catalyst responded to Sigma Pseudo Explosive Scent; TiON/PAN +Pd catalyst has no response to Sigma Pseudo Explosive Scent. All three compositions were sensitive to cyclohexane.

Example 31

Electroceramics

This example is from U.S. patent application Ser. No. 09/153,418 which was incorporated in this specification and is herewith presented for convenience.

Electroceramics are important components of numerous products for electrical, communication, electronic, and sensor/actuator industries. Illustrative examples include capacitors, inductors, resistors, insulators, antennae, interference filters, MMIC, transducers, transformers, electromagnets, piezo devices, packaging, batteries, and displays. Significant improvements in existing electroceramics or novel formulations of electroceramics can make significant impact on a wide range of products.

It is well established in electroceramic device industry that pure, single or two metal oxides rarely offer a property envelope that meets all the needs of real life applications. It is necessary to add dopants, substituents, and additives to stabilize the performance and reliability of the device over variations in temperature, variations in voltage, variations in frequency, and manufacturing and other process conditions. For example, in capacitors, the following additives are routinely added: $CaTiO_3$, $SrTiO_3$, $TiO_2$, $ZrO_2$, rare earth oxides, (e.g., as donor dopants, sintering aids, and Curie point shifters). Additions of additional metal ions can also have a profound effect on the dielectric constant of the material as evidenced by Table 4.

TABLE 4

Dielectric Constants as a Function of Material Chemistry

| EIA rating | Dielectric Constant | $BaTiO_3$ content (wt %) | Density (g/cm$^3$) |
|---|---|---|---|
| NPO | 75 | 10-50 | 4.20 |
| BX, X7R | 3000 | 90-98 | 5.80 |
| Z5U | 8000 | 84-94 | 5.80 |
| Z5V | 18000 | 80-94 | 5.80 |

It is common in practice to discover satisfactory electroceramic formulations by a trial-and-error approach. The cost of developing such formulations is high and thus, novel applications and novel, high performance, reliable electroceramic devices are slow and expensive to develop and manufacture. This invention addresses this limitation through the use of combinatorial screening.

For electroceramics screening, an electrode (Ag/Pd) array of 625 (15×15) elements is printed. Next, $BaTiO_3$, $SrTiO_3$, $TiO_2$, $WO_3$, NdO, $Fe_2O_3$, and $MnO_2$ films are printed using a piezo-array inkjet printer controlled by a PC. The array synthesized is a Taguchi Statistical Set derived from seven oxides and eight concentration levels (2%, 8%, 20%, 40%, 60%, 80%, 92%, 98%). This is followed by printing the second layer of the electrode. The electrode ends are terminated. The array is then be cured and sintered to 1150° C. at a 10° C./min ramp rate. This ensures the removal of organics, microstructural integrity, solid state synthesis reaction completion, and defect elimination in the layers of each element.

The performance of each element is determined in rows and columns format by measuring the capacitance and temperature coefficient of capacitance (TCC) using a cap bridge; impedance response as a function of frequency is measured using a Hewlett Packard impedance analyzer (HP4191A). The loss factor is determined. A row and column format testing is chosen to reduce the time to parallel test the elements. Each element could be screened one element at a time instead, but that would be time consuming and expensive. By vector searching the array, promising vectors of the array can be discovered first and these can then be related to cross vectorial analysis to identify the candidate elements that have high performance in both a row and a column. Note that, since each vector consists of capacitors in parallel, the capacitance of each vector j can be modeled as:

$$C_j = \frac{1}{\frac{1}{\sum_i C_{ij}}}$$

where $C_{ij}$ is the capacitance of array element ij. If row i and column j both offer promising characteristics, element ij is an expected candidate for further specific screening and testing. A heating pad and a thermistor layer embedded underneath each capacitor element can be used to maintain and monitor the temperature. This assembly can assist the determination of elements' TCC. The voltage coefficient of capacitance and dissipation factor can also measured.

The breakdown strength of the components is determined by increasing the applied voltage until a direct short occurs. This breakdown in irreversible and determines the absolute maximum voltage at which the device can be used. A Hipotronics HD 100 series HIPOT tester can used for this purpose, for example. To eliminate the possibility of arcing across the part at high voltages, it is preferred that the part be immersed in dielectric fluid before the voltage is applied. Destructive tests such as this, of course, should be done after nondestructive testing is complete.

Example 32

Optical Switches

This example is from U.S. patent application Ser. No. 09/153,418 which was incorporated in this specification and is herewith presented for convenience.

In many substances, changes in chemical composition, pressure or temperature can induce metal-to-insulator transitions. Although dramatic changes in optical and electrical properties accompany such transitions, their interpretation is often complicated by attendant changes in crystallographic structure. Yttrium, lanthanum and the trivalent rare-earth elements form hydrides that also exhibit optical property transition. A shiny mirror-like thin film of yttrium or lanthanum with a layer of palladium through which hydrogen can diffuse can turn transparent when it absorbs hydrogen. But, once the Y or La thin film has been hydrogenated, it does not decompose readily. Thus, the transparent metal hydride film can not easily be turned back to the opaque state by dehydrogenation. For this reason, the interesting optical properties of Y and La metal hydrides have not found immediate application. However, a number of binary and ternary reversible hydrogen storage alloys have been studied and developed in past two decades. By adopting combinatorial approach, a large group of metal hydrides can be synthesized and their optical properties investigated in a relatively short period.

In these embodiments of the invention, optical switchable thin films are synthesized in a sputtering system, for example one that offers deposition, etching and plasma processing capability. Optical quartz plates with about 0.5-1.0 mm thickness are used as the substrates. A stainless steel foil is used to fabricate the physical masks. The libraries are generated by overlaying a primary physical mask, containing a grid of 16 openings (or any desired number), with a series of secondary masks. The thickness of each member may vary depend on the individual composition. A 20 nm Pd cap layer is coated on all library members homogeneously. The remaining area on the substrate, which must reflect light completely, is coated by gold deposition with third blanket mask. A 16-member binary library derived from Ni, La, Ce, Y and Zr is synthesized; in this example, each site is 2 mm by 2 mm in size, but this can reduced if desired.

The composition of individual binary alloy films is determined by the thickness of each component deposition layer. For example, a 100 nm La film overlapping a 100 nm Ni film is expected to produce the binary alloy LaNi after sintering. The library is then sintered to ensure the formation of the desired binary alloys by solid state reaction. XRD can be used to verify the crystal structure and phase composition. The thickness of films is measured by SEM.

The combinatorial library of optical switch materials is then investigated to determine how their optical properties are influenced by hydrogen. In this example, the experimental investigation focuses on optical switch capability and, in particular, on reversibility.

To verify the optical switch capability of the different alloy films, the thin film array (library) is placed in a dark chamber that can be evacuated by a vacuum pump and filled with hydrogen at a desired pressure. A visible light beam is introduced that hits the thin film array through the optical window of the dark chamber. A photodetector (digital camera) monitors the back side of the array. When hydrogen is introduced into the dark chamber gradually, the alloys in the array react with it to form different metal hydrides with differing transparencies. The photodetector captures the light transmitted through the metal hydride films and convert the signals into digital data. Analyzing the data collected, the optical switch capability of each individual alloy is assessed. The optimal composition of alloy is one that offers largest optical switch capability at moderate hydrogen pressure.

The reversibility of optical switching, e.g., two direction switching, is an important optical property for some potential applications, such as hydrogen sensors and radiation shield devices. To determine or optimize a material for such a device, after hydrogenation, the hydrogen is evacuated from the dark chamber by a vacuum pump. The metal hydrides in the library decompose to release hydrogen (an embedded heater underneath each element can be used to assist the decomposition, or the test apparatus can be placed inside a furnace). The transparency of the films decreases during the de-hydrogenation process. The photodetector observes and records the decrease in the film transparency. This decrease is expected vary for each film, because of the different thermodynamic stabilities of the individual library members.

Example 33

Catalysts

This example is from U.S. patent application Ser. No. 09/153,418 which was incorporated in this specification and is herewith presented for convenience.

This example illustrates the use of this invention for discovery of catalysts. Alternative catalytic materials have the potential to exert an enormous impact on the chemical and energy industries. These industries are two of the largest in the U.S., with individual sales exceeding several hundred billion dollars. About 90% of chemical and energy processes and over 20% of U.S. industrial products in general involve catalysis.

Breakthroughs in catalytic materials can lower operating costs associated with energy, raw materials and environmental improvement; reduce capital costs for investment in new processing technologies; accelerate discovery of competitive and environmentally superior process chemistries; enable novel products and technologies; and reduce dependence on precious metals for catalytic applications. Clearly, the significance of innovation in catalytic materials is high. Combinatorial screening offers an opportunity to rapidly develop new catalytic materials.

In this embodiment of the invention, first a microfabricated reactor array is formed. (The described procedure may also be performed using a macro-array of reactors). This structure features a parallel array of reactors each of which is identical to other elements in the array. The dimensions of the array are designed to reduce pressure drop, ensure flow uniformity in each reactor, prevent short circuiting, enable temperature control, and provide for an architecture that favors the analysis of reaction being studied and the reliability of the analysis.

One method is to build the reactor from silicon micromachining; that is, by first forming an array of reactor cavities (pits) that can hold known and desired quantity of catalyst candidates. The cavities are connected to the product side surface with holes. Each pit is filled with a nanostructured or other high surface area form of a candidate material and covered with a mating part micromachined to ensure isolation of each reactor cavity and provided with holes to connect the cavity to the feed side. The silicon micromachining technique can also be used to add heaters underneath or around each reactor cavity and provide for sensors, optics, or microelectronics for analysis of the reaction.

The silicon micromachining technique is limited by the material limitations of silicon. Many side reactions can occur at high temperatures and refractory reactor arrays are desirable in these applications. Anodized alumina is an excellent candidate for building such microfabricated reactor arrays. Anodized alumina naturally forms aligned pores that can be utilized for carrying feed into the reactor cavity and to carry products out of the reactor cavity, as more fully described in commonly assigned U.S. application Ser. No. 09/103,203, incorporated herein by reference. Other self-assembled or desktop manufactured or mold manufactured refractory ceramics can be utilized to form such reactor cavity arrays as well. Micromachined arrays of one material can also be used as imprints and molds to form reactor arrays from other materials.

In each case, the number of array elements is kept greater than 1, more preferably greater than 100, even more preferably greater than 10,000, and most preferably greater than 1,000,000. The array so prepared has in each cavity a nanopowder or another high specific surface area form of a potential catalyst material. If the objective is catalyst discovery, the cavities are filled with an array of different candidate material formulations, e.g., doped or undoped, inorganic or organic, homogeneous or heterogeneous, porous or non-porous, and stoichiometric or non-stoichiometric. The array elements can be arranged in symmetry or stacked. Reactor cavities may be arranged in series and may be of various shapes and sizes. Valves and control structures may be micromachined or otherwise added to assist control of individual reactor cavity. If the objective is optimization of a catalyst material, then a row or column of cavities may show a gradient in composition as desired, where the gradient is incremental or arranged according to statistical pattern such as Taguchi search and others that are known to those skilled in the art.

The testing for catalytic activity is done using parallel screening search technique such as the bisectional search, the golden mean search, or the Fibonacci search. To illustrate without limiting the scope, this example discusses the bisectional search for the discovery of a catalyst for a gas phase reaction for which no catalyst is known. To begin, half of the array is isolated and completely covered to prevent any interaction with feed gases. The collective response of the catalyst candidates in the other half is collected by flowing the feed gas through and collecting the product gas. The product gas is analyzed. If the product gases show no signature of the desired species, it is concluded that the candidate catalysts in tested half do not have any potential candidate catalyst that is desired. Any catalysts within the candidate set must be present in the untested half.

On the other hand, if a desired product species is detected in the tested half, then it is concluded that one or more of the candidate formulations in that half have the desired catalytic activity. In this situation, half of the tested half (one quarter of the array) is further covered and isolated and the remaining quarter tested. If the test shows that the tested quarter has no signature of the desired species, it is concluded that the candidate catalysts in tested quarter does not have any potential candidate catalyst that is desired. It is furthermore concluded that the active catalyst must be in the other quarter given the fact that the previous test had indicated that at least one formulation is catalytically active. It is to be noted that a positive test in one section does not necessarily mean that the other section is unpromising and negative. The objective and correct conclusion that can be drawn with certainty is the confirmed absence of activity. In each step, the search is bisectionally focused on smaller and smaller sections that give positive results, while the sections that give negative results are eliminated. Such a bisectional search quickly can help eliminate unpromising candidates.

The isolation technique in parallel search techniques can be an external mask or an embedded or attached valve that is electromagnetically, mechanically, magnetically, thermally, or otherwise switched into on and off positions. A preferred search technique is the golden mean search. The mask can be simple or complex patterned. An example of simple pattern is closed arc or a rectangle. An example of complex pattern is hole filled arc or hole filled rectangle. The preferred pattern is simple.

In case of optimization of catalytic materials, a similar search method may be used. However, then each section must be searched and the decision to focus should be based on relative performance of each section. Better performing sections should be naturally selected over more poorly performing sections. Sections that fail to perform should be eliminated from the selection process. Sections that fail to perform may be reused as starting materials, by reformulating, doping, heating, reacting and/or otherwise modifying the array, and then retesting for activity.

With automated valves, a control unit may be integrated in the search process. In such architecture, sections of feed valves may be closed and the product gases analyzed on-line or in batches, the preferred method being on-line. When undesired changes in product composition (selectivity and yield) are detected as a section is brought on-line, feed valves in the said section are closed or left open one by one automatically. A valve is left open if the change in product composition is desired, and the valve is closed if the change in product composition is undesired or indifferent. Such natural selection of populations can help eliminate weaker candidates and identify stronger candidates to meet the search and optimization objectives.

The benefit of using mathematical search algorithm such as the golden mean search is that the number of actual tests needed is reduced by more than half, often less than a square root of the actual number of candidates. Thus, if the library consists of 10,000 elements, routine one-by-one search would require 10,000 tests, while the search algorithms disclosed will typically require about less than 5,000 tests and often about 100 tests. In case of a library of 1,000,000 elements, the search algorithms disclosed will often require about 1,000 tests.

The technique disclosed can be used even when the actual testing of product may not be simple. In such cases, secondary products or effects may be tested. For example, the temperature of the catalyst, the radiation from catalyst, the concentration of a byproduct (e.g., hydrogen, water, carbon dioxide, ammonia, carbon monoxide, nitrogen, or other species), the pressure of the reaction gases, the flow rate from the reactor cavity, the electrochemical activity, or the nuclear radiation from the reaction may be monitored. The search methods described above can be applied to these measurements as well as to direct measurements of the desired product species. When sensors for direct monitoring of desired products or direct monitoring of byproducts or effects are available and can be embedded, attached, or functionally positioned in or near the micromachined reactor, the search may be completed instantly by monitoring the sensor response as the feed flows through the reactor array.

The catalyst screening method may be applied to search of catalysts for liquid phase reactions, homogeneous reactions, solid phase reactions, biochemical reactions, or complex reactions. This technique can be used for searching and discovering and optimizing biocatalysts or pharmaceuticals or molecules with bioactivity.

Example 34

Resistors

This example is from U.S. patent application Ser. No. 09/153,418 which was incorporated in this specification and is herewith presented for convenience.

Resistors that do not vary with changes in environment are used in numerous electrical and electronic products. Resistors that do vary with changes in its environment are used in sensing applications. Illustrative, but not limiting, examples of sensing applications include resistors whose resistance changes with radiation exposure (photoconductors, photodetectors, bolometers, and radiation sensors), electrical field (electromagnetic sensors), magnetic field (data storage read heads), chemicals (chemiresistive sensors), pressure (piezoresistive sensors), and heat flow (thermistors). This example illustrates how this invention can be applied to both types of resistors.

Two sets of inks were prepared for the studies. One set consisted of metal nanopowder doped resistive inks and the second of ceramic nanopowder doped resistive inks. In each of the preparations, the ink and a selected amount of additive were weighed out and mixed together with a mortar and pestle. Table 5 shows the composition of the inks.

TABLE 5

Compositions of Inks for Combinatorial Studies

| Set 1 | Set 2 |
|---|---|
| Resistive Ink ESL 3910 | Resistive Ink ESL 3910 |
| 20 wt % Antimony doped ESL 3910 | 5 wt % $Al_2O_3$ doped ESL 3910 |
| 20 wt % Palladium doped ESL 3910 | 10 wt % $Al_2O_3$ doped ESL 3910 |
| 20 wt % 95/5 Silver/Palladium doped ESL 3910 | 15 wt % $Al_2O_3$ doped ESL 3910 |

Six arrays of each set of inks were screen printed on to a previously printed Silver/Platinum electrode. All screen printing was accomplished using a semi-automatic screen printer.

The prepared inks were printed over each electrode one composition at a time. The printed material was dried at 100° C. between the printing of each composition. Once the array was completely printed and dried it was fired at 850° C. for 10 minutes.

To test the arrays a Fluke multi-meter was utilized and the resistance of each element was recorded. Tables 6 and 7 give the results of the arrays based on the resistive ink.

TABLE 6

Combinatorial Studies, Set 1. Results are given in Ohms.

| Material | 1 | 2 | 3 | 4 | 5 | 6 | Ave. |
|---|---|---|---|---|---|---|---|
| ESL 3910 | 1.4 | 1.3 | 1.3 | 1.3 | 1.3 | 1.4 | 1.33 |
| Antimony doped ESL 3910 | 6.5 | 5.5 | 6.0 | 10.3 | 10.3 | 8.2 | 7.80 |
| Palladium doped ESL 3910 | 1.5 | 1.4 | 1.4 | 1.5 | 1.5 | 1.4 | 1.45 |
| Ag/Pd doped ESL 3910 | 1.0 | 1.0 | 1.0 | 1.0 | 1.0 | 1.0 | 1.00 |

TABLE 7

Combinatorial Studies, Set 2. Results are given in Ohms.

| Material | 1 | 2 | 3 | 4 | 5 | 6 | Ave. |
|---|---|---|---|---|---|---|---|
| ESL 3910 | 1.3 | 1.2 | 1.2 | 1.2 | 1.3 | 1.1 | 1.22 |
| 5% $Al_2O_3$ doped ESL 3910 | 1.3 | 1.3 | 1.2 | 1.2 | 1.2 | 1.2 | 1.24 |
| 10% $Al_2O_3$ doped ESL 3910 | 1.8 | 1.3 | 1.3 | 1.2 | 1.3 | 1.3 | 1.37 |
| 15% $Al_2O_3$ doped ESL 3910 | 1.8 | 1.8 | 2.1 | 1.5 | 1.8 | 1.8 | 1.80 |

The parallel testing of Set 1 (Table 6) indicated that adding metal powder to the resistive ink can be used to tailor the resistance of formulation. The screening led to the discovery that antimony had an abnormally large effect, increasing the resistance approximately five times more than the other tested materials. The screening also indicated that the addition of silver decreases the resistance 25%. The addition of palladium produced a minor change in resistance. Thus, in any application where resistance of ink is to raised, the screening discovered that antimony is the preferred choice. In any application where resistance of ink is to lowered, silver is the preferred choice.

The parallel testing of Set 2 (Table 7) indicates that adding alumina powder to the resistive ink can also tailor the resistance of the ink. The screening led to the identification that alumina nanopowders have statistically insignificant effect on the resistance of the ink at levels below 5%. The addition of ceramic powder above 5% can be used to optimize the resistance of the resistive ink.

Example 35

Thermoelectric Materials

This example is from U.S. patent application Ser. No. 09/153,418 which was incorporated in this specification and is herewith presented for convenience.

Thermoelectric devices convert thermal energy into electrical energy or electrical energy into thermal energy. Inherent advantages of these devices include portability, reliability, simplicity, flexibility, quietness, and environmental benignity. High-performance thermoelectric materials can enable the manufacture of thermoelectric refrigerating devices with efficiencies above those achievable with chlorofluorocarbon based compressors. This can help launch the production of all solid state, high reliability, low power, low vibration crycoolers for advanced electronics and detectors, as well as refrigerator units with no pressure vessel, moving parts, or acoustic signature. In addition, such materials may also be used for thermoelectric power generation from either a fuel based heat source or for exhaust heat recovery. The biggest obstacle for thermoelectric devices to be widely used is the low efficiency of thermal/electrical energy conversion limited by thermoelectric materials with which these devices are made. The key to successful commercialization of thermoelectric devices, therefore, to a large degree, depends on the development of high-performance thermoelectric materials.

The performance of the thermoelectric material is generally evaluated through its so-called the figure-of-merit, which is defined as $$Z = \frac{\alpha^2 \sigma}{\lambda}$$

where $\alpha$ is the Seebeck coefficient, $\lambda$ the thermal conductivity, and $\sigma$ the electric conductivity of the material. The dimensionless figure-of-merit ZT is commonly used. A high-performance thermoelectric material should have a low thermal conductivity to prevent a significant portion of the heat from flowing down the temperature gradient, a high electric conductivity to reduce the energy loss due to the Joule heating, and a high Seebeck coefficient to have high efficiency of thermal/electric energy conversion. That is, it should have a very high ZT.

Efforts to develop high-performance or high ZT thermoelectric materials date back many years. Many material systems have been explored one at a time, with a focus on increasing the electrical conductivity and decreasing thermal conductivity. However, the nature of these materials and correlation of thermal and electrical conductivity place limits on possible improvement of the figure-of-merit of the traditional thermoelectric materials. All the currently-available thermoelectric materials have figures-of-merit less than or equal to 1 for both room temperature and cryogenic applications.

Examples compositions include bismuth telluride, bismuth selenide, bismuth antimonide, quasicrystalline alloys, skutterudites, and complex formulations of various chalcogenides and alloys. There is a need for formulations that show ZT higher than 1.0, preferably higher than 2.0, and even more preferably higher than 3.0, and most preferably with Coefficient of Performance that would make solid state devices functioning close to Carnot efficiencies.

The emergence of nanostructured materials, however, opens up a new chapter in designing and synthesizing advanced materials. When the dimension of the material is reduced to 2-, 1-or even 0-dimensions, the classic physical laws based on Newtonian physics, which govern the material's behavior, have to be replaced by those based on quantum mechanics. Thus, nanostructured materials offer many novel properties which can not be matched by traditionally-formed materials. This recently emerging technology offers drastic improvement in materials performance-such as in thermoelectric applications, as described in copending and commonly assigned U.S. patent application Ser. No. 09/103,203, incorporated herein by reference. Combinatorial screening can be used to discover and optimize nanostructured thermoelectric compositions in particular and novel compositions in general.

Nanomaterials are ideally suited for the search of novel thermoelectric formulations because nanomaterials are a group of materials which have many unique properties, including thermoelectric properties, unmatched by traditional materials. The unique nano-confined microstructure offers the following unique features:

1. Much lower thermal conductivity. In a nanostructured material, each grain is so small that the mean free path of phonons is solely limited by the grain size. Thus, the thermal conductivity is proportional to the grain size. A nanostructured material with average grain size of 10 nm would have a thermal conductivity 100 times as low as that of the material in traditional form (with a grain size of ~1000 nm);

2. Greater Seebeck coefficient. Nano-size particles, with diameter of ~10 nm, are quasi-0-dimensional materials. The quantum confinement will be dominant in determining its thermoelectric properties. It is anticipated that in nanometer range, the Seebeck coefficient should be much greater than that of the micron-scale material.

3. Higher electrical conductivity. The large number of grain boundaries reduces the barrier for electrons to across into the neighboring grain, so that the overall electrical conductivity of the proposed nanostructured thermoelectric material may not be lowered by grain boundary scattering of electrons within each grains.

4. Figure-of-merit ZT>>1. The lower thermal conductivity, higher Seebeck coefficient and higher electrical conductivity of the proposed thermoelectric material will yield a much higher figure-of-merit. For a material which has a figure-of-merit close to 1 in its micron-scale form, the proposed design of the material is expected to have a figure-of-merit much greater than 1.

5. Superior mechanical performance. The ultra-fine microstructure of nanostructured materials leads to high mechanical strength, superior plasticity and excellent toughness. The superior mechanical performance will make nanostructured thermoelectric materials stronger, more reliable, and more economical in fabrication and post-processing (such as machining).

6. Low processing cost. Nanomaterials can be densified at much lower temperatures and much shorter cycle times than materials in the traditional form, because of their high specific surface area, resulting in reduction of recrystallization temperature, enhanced diffusivity and thus sinterability.

7. Integrability with Existing Technology. Micron-scale powders are currently used by the industry to make thermoelectric devices. The invention uses nanostructured powders—an approach that enables facile integration of the proposed technology into existing thermoelectric device technology.

One method that can be used for combinatorial screening is to begin by preparing a library of combinatorial formulations, preferably in nanostructured form. The resistance of the library can be measured by a technique such as that described in Example 34, and the thermal conductivity of the formulation through the thickness would be measured using radiative techniques. For example, an array of radiation (infrared or suitable wavelength) sensors could monitor surface radiation. Alternatively, thermistors may be embedded underneath the thermoelectric film to sense the temperature gradient over each element while the other face of the films is exposed to uniform temperature. It is important to measure the electrical and thermal resistance simultaneously to screen and optimize the thermoelectric formulation. The analysis may also be done with a probe array structure used in combination with scanning microscopes and software to drive the probe array and interpret the results thereof.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A non-stoichiometric nanomaterial comprising two or more elements having a composition different than that required for stoichiometric bonding between the two or more elements, the composition represented by the formula:

$M_{n/p}Z_{1-x}$ wherein M comprises an element that can lower its free energy by chemically bonding with Z;
wherein Z comprises a chalcogen;
wherein n and p are integers greater than or equal to 1;
wherein $0.01<x<0.99$; and
wherein a value for a selected material property of the non-stoichiometric nanomaterial is greater than 10% different from a value for the same property for a stoichiometric form of the nanomaterial.

2. The non-stoichiometric nanomaterial of claim 1, wherein M is selected from the group consisting of: Ti, Mn, Fe, Ni, Zn, Cu, Sr, Y, Zr, Ta, W, Sc, V, Co, In, Li, Hf, Nb, Mo, Sn, Sb, Al, Ce, Pr, Be, Np, Pa, Gd, Dy, Os, Pt, Pd, Ag, Eu, Er, Yb, Ba, Ga, Cs, Na, K, Mg, Pm, Pr, Ni, Bi, Tl, Ir, Rb, Ca, La, Ac, Re, Hg, Cd, As, Th, Nd, Th, Md, and Au.

3. The non-stoichiometric nanomaterial of claim 1, wherein $0.02<x<0.98$.

4. The non-stoichiometric nanomaterial of claim 1, wherein $0.05<x<0.95$.

5. The non-stoichiometric nanomaterial of claim 1, wherein the domain size of the material is less than 5 times the mean free path of electrons in the material.

6. The non-stoichiometric nanomaterial of claim 1, wherein the domain size of the material is less than 100 nanometers.

7. The non-stoichiometric nanomaterial of claim 1, wherein the nanomaterial comprises two or more elements M that can lower their free energy by chemically bonding with Z.

8. The non-stoichiometric nanomaterial of claim 1, wherein the nanomaterial comprises more than one element Z.

9. The non-stoichiometric nanomaterial of claim 1, wherein the nanomaterial comprises more than one element M and more than one element Z.

10. The non-stoichiometric nanomaterial of claim 1, wherein the nanomaterial comprises a multimetallic nanopowder having an aspect ratio in a range of 1-25.

11. The non-stoichiometric nanomaterial of claim 1, wherein the nanomaterial comprises a polymetallic nanopowder comprising at least three metals and at least one chalcogen anion, and having a minimum dimension of less than 100 nm and an aspect ratio of 25 or less.

12. The non-stoichiometric nanomaterial of claim 1, wherein the nanomaterial comprises a nanofiller dispersed in a polymer matrix, thereby forming a nanostructured composite material.

13. A coating composition comprising the non-stoichiometric nanomaterial of claim 1.

14. A nanostructured composite material comprising:
a polymer matrix; and
a nanofiller dispersed in the polymer matrix;
wherein the nanofiller comprises a non-stoichiometric nanomaterial comprising two or more elements having a composition different than that required for stoichiometric bonding between the two or more elements, the composition represented by the formula:

$M_{n/p}Z_{1-x}$ wherein M comprises an element that can lower its free energy by chemically bonding with Z;
wherein Z comprises a chalcogen;
wherein n and p are integers greater than or equal to 1; and
wherein $0.01<x<0.99$; and
wherein a value for a selected material property of the nanostructured composite material comprising the nanofiller is at least 20% different from a value for the same property for an otherwise identical composite material comprising a micron-scale filler.

15. The nanostructured composite material of claim 14, wherein the nanofiller comprises a polymer coated nanofiller.

16. The nanostructured composite material of claim 14, wherein the nanofiller comprises a monomer coated nanofiller.

17. The nanostructured composite material of claim 14, wherein the composite material comprises a coating composition.

18. The nanostructured composite material of claim 14, wherein M is selected from the group consisting of: Ti, Mn, Fe, Ni, Zn, Cu, Sr, Y, Zr, Ta, W, Sc, V, Co, In, Li, Hf, Nb, Mo, Sn, Sb, Al, Ce, Pr, Be, Np, Pa, Gd, Dy, Os, Pt, Pd, Ag, Eu, Er, Yb, Ba, Ga, Cs, Na, K, Mg, Pm, Pr, Ni, Bi, Tl, Ir, Rb, Ca, La, Ac, Re, Hg, Cd, As, Th, Nd, Th, Md, and Au.

19. The nanostructured composite material of claim 14, wherein $0.02<x<0.98$.

20. The nanostructured composite material of claim 14, wherein $0.05<x<0.95$.

21. The nanostructured composite material of claim 14, wherein the domain size of the material is less than 5 times the mean free path of electrons in the material.

22. The nanostructured composite material of claim 14, wherein the domain size of the material is less than 100 nanometers.

23. The nanostructured composite material of claim 14, wherein the nanomaterial comprises two or more elements M that can lower their free energy by chemically bonding with Z.

24. The nanostructured composite material of claim 14, wherein the nanomaterial comprises more than one element Z.

25. The nanostructured composite material of claim 14, wherein the nanomaterial comprises more than one element M and more than one element Z.

26. The nanostructured composite material of claim 14, wherein the nanomaterial comprises a multimetallic nanopowder having an aspect ratio in a range of 1-25.

27. The nanostructured composite material of claim 14, wherein the nanomaterial comprises a polymetallic nanopowder comprising at least three metals and at least one anion, and having a minimum dimension of less than 100 nm and an aspect ratio of 25 or less.

28. A non-stoichiometric nanomaterial comprising two or more elements having a composition different than that required for stoichiometric bonding between the two or more elements, the composition represented by the formula:

$$M_{n/p}Z_{1-x}$$

wherein M comprises an element that can lower its free energy by chemically bonding with Z;

wherein Z comprises an element selected from the group consisting of B, C, Si, N, P, O, S, Se, Te, and H;

wherein n and p are integers greater than or equal to 1;

wherein 0<x<1; and wherein a value for a selected material property of the non-stoichiometric nanomaterial is greater than 10% different from a value for the same property for a stoichiometric form of the nanomaterial.

29. A nanostructured composite material comprising:

a polymer matrix; and a nanofiller dispersed in the polymer matrix;

wherein the nanofiller comprises a non-stoichiometric nanomaterial comprising two or more elements having a composition different than that required for stoichiometric bonding between the two or more elements, the composition represented by the formula:

$$M_{n/p}Z_{1-x}$$

wherein M comprises an element that can lower its free energy by chemically bonding with Z;

wherein Z comprises an element selected from the group consisting of B, C, Si, N, P, O, S, Se, Te, and H;

wherein n and p are integers greater than or equal to 1;

wherein 0<x<1; and wherein a value for a selected material property of the nanostructured composite material comprising the nanofiller is at least 20% different from a value for the same property for an otherwise identical composite material comprising a micron-scale filler.

* * * * *